United States Patent
Mollicone et al.

(10) Patent No.: US 8,812,428 B2
(45) Date of Patent: Aug. 19, 2014

(54) SYSTEMS AND METHODS FOR ASSESSMENT OF FATIGUE-RELATED CONTEXTUAL PERFORMANCE USING HISTORICAL INCIDENT DATA

(75) Inventors: Daniel Joseph Mollicone, Seattle, WA (US); Christopher Grey Mott, Seattle, WA (US)

(73) Assignee: Pulsar Informatics, Inc., Philadelphia, PA (US)

( * ) Notice: Subject to any disclaimer, the term of this patent is extended or adjusted under 35 U.S.C. 154(b) by 151 days.

(21) Appl. No.: 13/235,956

(22) Filed: Sep. 19, 2011

(65) Prior Publication Data

US 2012/0089553 A1   Apr. 12, 2012

Related U.S. Application Data

(60) Provisional application No. 61/384,673, filed on Sep. 20, 2010.

(51) Int. Cl.
| G06F 9/44 | (2006.01) |
| G06F 19/00 | (2011.01) |
| G06N 7/00 | (2006.01) |
| G06N 5/04 | (2006.01) |

(52) U.S. Cl.
CPC ........ *G06F 19/3431* (2013.01); *G06F 19/3437* (2013.01); *G06N 7/005* (2013.01); *G06N 5/048* (2013.01)
USPC ............................................. 706/52; 600/300

(58) Field of Classification Search
CPC ................................ G06N 5/048; G06N 7/005
USPC ............................................. 706/52; 600/300
See application file for complete search history.

(56) References Cited

U.S. PATENT DOCUMENTS

| 5,433,223 | A | 7/1995 | Moore-Ede et al. |
| 5,682,882 | A | 11/1997 | Lieberman |
| 6,496,724 | B1 | 12/2002 | Levendowski et al. |
| 6,511,424 | B1 | 1/2003 | Moore-Ede et al. |
| 6,516,222 | B2 | 2/2003 | Fukuda |
| 6,530,884 | B2 | 3/2003 | Balkin et al. |
| 6,553,252 | B2 * | 4/2003 | Balkin et al. .................. 600/544 |
| 6,579,233 | B2 | 6/2003 | Hursh |

(Continued)

FOREIGN PATENT DOCUMENTS

| WO | WO2009/052633 | 4/2009 |
| WO | WO 2009052633 A1 * | 4/2009 |

OTHER PUBLICATIONS

Dongen, Comparison of Mathematical Model Predictions to Experimental Data of Fatigue and Performance; Aviation, Space, and Environmental Medicine, vol. 75, No. 3, Section II, Mar. 2004.*

(Continued)

*Primary Examiner* — Jeffrey A Gaffin
*Assistant Examiner* — Robert H Bejcek, II
(74) *Attorney, Agent, or Firm* — Damian M. Biondo, Esq.

(57) ABSTRACT

Disclosed herein are methods for transforming numerical output of mathematical-fatigue models into contextual performance metrics, including without limitation, performance, incident and/or accident-related metrics associated with particular activities and/or with particular environments, such as but not limited to: the number and severity of injuries or cost of repairs associated with a particular incident, increases in insurance premiums, a performance rate, an error rate and/or the like.

33 Claims, 9 Drawing Sheets

(56) References Cited

U.S. PATENT DOCUMENTS

| | | | |
|---|---|---|---|
| 6,740,032 | B2 | 5/2004 | Balkin et al. |
| 6,743,167 | B2 | 6/2004 | Balkin et al. |
| 6,894,606 | B2 | 5/2005 | Forbes et al. |
| 7,189,204 | B2 | 3/2007 | Ni et al. |
| 7,192,401 | B2 * | 3/2007 | Saalasti et al. ............ 600/500 |
| 7,824,888 | B2 | 11/2010 | Kondo |
| 7,860,561 | B1 | 12/2010 | Modarres |
| 2003/0018242 | A1 * | 1/2003 | Hursh et al. ............ 600/300 |
| 2005/0154634 | A1 | 7/2005 | Konop |
| 2006/0200008 | A1 * | 9/2006 | Moore-Ede ............ 600/300 |
| 2009/0132332 | A1 | 5/2009 | Belenky et al. |

OTHER PUBLICATIONS

Reifman, Alternative Methods for Modeling Fatigue and Performance; Aviation, Space, and Environmental Medicine, vol. 75, No. 3, Section II, Mar. 2004.*

Dinges, D. F. and Powell, J. W. "Microcomputer analyses of performance on a portable, simple visual RT task during sustained operations." Behavior Research Methods, Instruments, & Computers 17(6): 652-655, 1985.

Johns, M. W., "A new method for measuring daytime sleepiness—the Epworth sleepiness scale." Sleep 14 (6): 54-545, 1991.

Akerstedt, T. and Gillberg, M. "Subjective and objective sleepiness in the active individual," International Journal of Neuroscience 52: 29-37, 1990.

Carskadon, M. W. et al., "Guidelines for the multiple sleep latency test—A standard measure of sleepiness." Sleep 9 (4): 519-524, 1986.

Mitler, M. M., Gujavarty, K. S. and Browman, C. P., "Maintenance of Wakefulness Test: A polysomnographic technique for evaluating treatment efficacy in patients with excessive somnolence." Electroencephalography and Clinical Neurophysiology 53:658-661, 1982.

Canisius, S. and Penzel, T., "Vigilance monitoring-review and practical aspects." Biomedizinische Technik 52(1): 77-82, 2007.

Neri, D. F., Oyung, R. L., et al., "Controlled breaks as a fatigue countermeasure on the flight deck." Aviation Space and Environmental Medicine 73(7): 654-664, 2002.

Peter Achermann, "The Two-Process Model of Sleep Regulation Revisited," 75:3 Aviation, Space, and Environmental Medicine A37-A43 (Mar. 2004).

Torbjorn Akerstedt, et al., "Accounting for Partial Sleep Deprivation and Cumulative Sleepiness in the Three-Process Model of Alertness Regulation," 25:2 Chronobiol. Intl. 309-319 (2008).

Mathias Basner and Joshua Rubenstein, "Fitness for Duty: A 3-Minute Version of the Psychomotor Vigilance Test Predicts Fatigue-Related Declines in Luggage-Screening Performance," 53:10 J. Occ. & Envir. Med. 1146-1154 (Am. Col. Occ. & Environ. Med., Oct. 2011).

A.A. Borbely, "A Two Process Model of Sleep Regulation," 1:3 Hum. Neurobiol. 195-204 (Oct. 1982).

Drew Dawson, et al., "Modelling Fatigue and the Use of Fatigue Models in Work Settings," 43 Accident Analysis and Prevention 549-564 (Elsivir Ltd. 2011).

David F. Dinges, "An Overview of Sleepiness and Accidents," 4:2 J. Sleep Res. 4-14 (Eur. Sleep Res. Socy. 1995).

Jillian Dorrian, Margaret Sweeney, and Drew Dawson, "Modelling Fatigue-Related Truck Accidents: Prior Sleep Duration, Recency, and Continuity," 9 Sleep & Biol. Rhythms 3-11 (Jap. Socy of Sleep Res. 2011).

"An Analysis of Fatal Large Truck Crashes," U.S. Dept. of Transp., Nat'l Highway Traffic Safety Admin., Technical Report DOT HS 809 569 (Jun. 2003).

Christopher Drake, et al., "The 10-Year Risk of Verified Motor Vehicle Crashes in Relation to Physiologic Sleepiness," 33:6 SLEEP 745-752 (2010).

Simon Folkard and Philip Tucker, "Shift Work, Safety, and Productivity," 53:2 Occ. Med. 95-101 (Socy. of Occ. Med. 2003).

Sean M. Kelly, et al., "Flight Controller Alertness and Performance During Spaceflight Shiftwork Operations," 3:1 Hum. Perf. Extrem. Environ. 100-106 (NASA Johnson Space Center, Sep. 1998).

Daniel J. Mollicone, et al., "Response Surface Mapping of Neurobehavioral Performance: Testing the Feasibility of Split Sleep Schedules for Space Operations," 63 Acta Astronomica 833-840 (Pergamon 2008).

Allan I. Pack, et al., "Characteristics of Crashes Attributed to the Driver Having Fallen Asleep," 27:6 Accid. Anal. & Prey. 769-775 (Elsevir Sci. Ltd. 1995).

Michael Smolensky, et al., "Sleep Disorders, Medical Conditions, and Road Accident Risk," 43 Acc. Anal. & Prey. 533-548 (Elsevir Sci. Ltd. 2011).

Jane C. Stutts, et al., "Driver Risk Factors for Sleep-Related Crashes," 35 Acc. Anal. & Prev. 321-331 (Elsevir Sci. Ltd. 2003).

Hans P. Van Dongen, et al., "Systematic Interindividual Differences in Neurobehavioral Impairment from Sleep Loss: Evidence of Trait-Like Differential Vulnerability," 27:3 SLEEP 423-433 (2004).

Hans P. Van Dongen, et al., "Mixed-Model Regression Analysis and Dealing with Interindividual Differences," 384 Meths. in Enzymology 139-171 (Elsevir Inc. 2004).

Hans P. Van Dongen, "Shift Work and Inter-Individual Differences in Sleep and Sleepiness," 23:6 Chronobiol. Intl. 1139-1147 (Informa Healthcare 2006).

Hans P. Van Dongen and Gregory Belenky, "Individual Differences in Vulnerability to Sleep Loss in the Work Environment," 47 Indus. Health 518-526 (2009).

Ann Williamson, et al., "The Link Between Fatigue and Safety," 43 Acc. Analy. & Prev. 498-515 (2011).

* cited by examiner

SYSTEMS AND METHODS FOR ASSESSMENT OF FATIGUE-RELATED CONTEXTUAL PERFORMANCE USING HISTORICAL INCIDENT DATA

RELATED APPLICATIONS

This application claims benefit of the priority of U.S. application No. 61/384,673, filed Sep. 20, 2010.

TECHNICAL FIELD

The invention relates to systems and methods for assessing contextual performance based on fatigue. Particular embodiments use one or more mathematical models that predict fatigue levels (model-predicted fatigue levels) of an individual for a time period of interest (e.g. a current and future time period) and then use information from an historical fatigue database to transform the model-predicted fatigue levels into a contextual performance metric.

BACKGROUND

Fatigue and alertness are related concepts—i.e. an increase in fatigue is typically associated with a decrease in alertness and vice-versa. Reduced levels of alertness and/or degraded performance associated with fatigue increases risk of being involved in accidents and/or reduced operational effectiveness that are often of concern in many industries, including without limitation transportation, health care, emergency response, manufacturing, mining, and space flight and in many activities, including without limitation participating in sports, driving, and/or the like. Factors that influence fatigue levels of individuals may include, without limitation, sleep history, time awake, time on task, work load, work schedule, light exposure, stimulant consumption, time of day, and/or the like. There is a general desire to predict the effects of fatigue on performance in terms contextually relevant performance metrics (e.g., risk of accident costing >$10,000) and, if possible, select appropriate countermeasures to improve such performance and reduce operational risk.

Mathematical models of fatigue allow computational approaches to predicting fatigue. Such models typically output a numerical score (a model-predicted fatigue level) that corresponds to an abstract representation of an individual's fatigue level. For example, a fatigue model may typically output a model-predicted fatigue level in the form of a number from zero (0) to one hundred (100). In some cases, such a model-predicted fatigue level may represent an individual's performance capacity as a percentage of some baseline (such as maximum capacity, normal capacity, or the like) determined when the individual is not affected by any fatigue-related factors. In some cases, the model-predicted fatigue level output by a mathematical fatigue model may be calibrated to a scale of another performance-related or fatigue-related test or physiological assay.

These types of model-predicted fatigue outputs do not easily translate into readily understandable performance metrics for real-world tasks. Without expert interpretation, it may be difficult to interpret the practical differences between an individual operating at a seventy-percent performance level versus a seventy-five-percent performance level.

There is a general desire to predict the effects of fatigue on performance in a manner that is relevant and easily understandable to those of non-expert skill in the field of fatigue science and fatigue management.

SUMMARY

Aspects of the invention provide systems and methods which use a mathematical model to predict fatigue levels (model-predicted fatigue levels) of an individual for a time period of interest (e.g. a current and future time period) and then use information from an historical fatigue database to transform the model-predicted fatigue levels into a contextual performance metric (CPM). The CPM may comprise one or more fatigue-related metrics specific to a particular context which may include one or more of: incident or accident-related metrics associated with particular activities and/or with particular environments; performance metrics associated with particular activities and/or with particular environments; and/or the like. Non-limiting examples of incident-related metrics associated with particular activities and/or environments include: a number of injuries associated with a particular incident which occurs while performing a particular activity or taking place in a particular environment, the cost of repair associated with a particular incident which occurs while performing a particular activity or taking place in a particular environment, the increase in insurance premiums associated with a particular incident which occurs while performing a particular activity or taking place in a particular environment, and/or the like. Non-limiting examples of performance metrics associated with particular activities and/or with particular environments include: a performance rate while performing particular activity or while operating in a particular environment, an error rate while performing particular activity or operating in a particular environment performance rates and/or the like.

One particular aspect of the invention provides a method for assessing the impact of fatigue on performance. The method comprises: determining an initial model-predicted fatigue level of an individual at an initial time; and transforming the initial model-predicted fatigue level into an initial contextual performance metric by applying a mapping function to the initial model-predicted fatigue level, the mapping function based at least in part on information contained in an historical fatigue database. The method may also comprise: determining an additional model-predicted fatigue level of the individual at an additional time, the additional time after the initial time and during a time interval of interest; and transforming the additional model-predicted fatigue levels into an additional contextual performance metric by applying the mapping function to the additional model-predicted fatigue level.

Another particular aspect of the invention provides a method for assessing the impact of fatigue on performance. The method comprises: determining an initial model-predicted fatigue level of an individual at an initial time; receiving schedule data for the individual in a future time interval of interest, the schedule data comprising at least one of: activity schedule data relating to times during the future time interval of interest that the individual is expected to be performing a particular activity; and sleep schedule data relating to times during the future time interval of interest that the individual is expected to be sleeping; determining a future model-predicted fatigue level of the individual at a future time, the future time after the initial time and during the future time interval of interest; and transforming the initial and future model-predicted fatigue levels into initial and future contextual performance metrics by applying a mapping function to the initial and future model-predicted fatigue levels, the mapping function based at least in part on information contained in an historical fatigue database. Determining the future model-predicted fatigue level may be based at least in part on the schedule data. The historical fatigue database may be populated by records, each record comprising: a contextual performance metric field comprising a contextual performance metric value obtained from one or more historical events; a fatigue level field comprising a fatigue level value obtained from one or more individuals associated with the one or more historical events; and one or more classifier fields comprising record-classification criteria associated with the one or more historical events.

Aspects of the invention may be provided as a computer program product embodied in non-transitory media and comprising computer-readable instructions which when executed by a suitable computer may cause the computer to perform any of the methods disclosed herein.

DETAILED DESCRIPTION

Figure 1A:
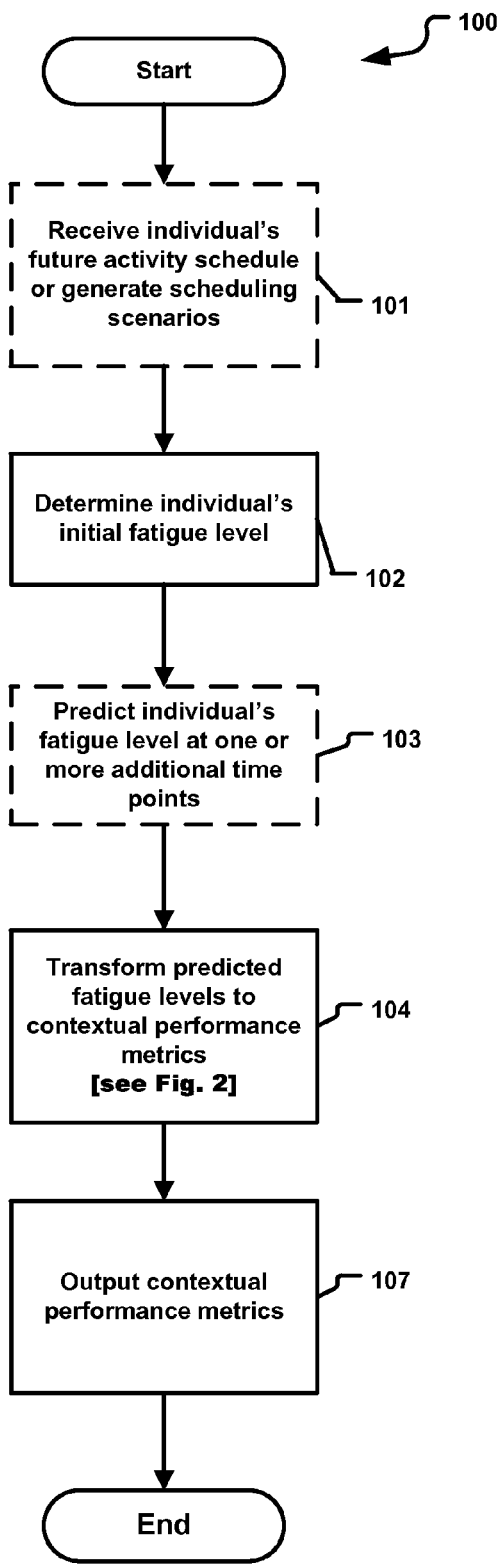
FIG. 1A is a flowchart showing a method for generating contextual performance metrics (CPMs) according to a particular embodiment.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Aspects of the invention provide systems and methods which use a mathematical model to predict fatigue levels (model-predicted fatigue levels) of an individual for a time period of interest (e.g. a current and future time period) and then use information from an historical fatigue database to transform the model-predicted fatigue levels into a contextual performance metric (CPM). The CPM may comprise one or more fatigue-related metrics specific to a particular context which may include one or more of: incident or accident-related metrics associated with particular activities and/or with particular environments; performance metrics associated with particular activities and/or with particular environments; and/or the like. Non-limiting examples of incident-related metrics associated with particular activities and/or environments include: a number of injuries associated with a particular incident which occurs while performing a particular activity or taking place in a particular environment, the cost of repair associated with a particular incident which occurs while performing a particular activity or taking place in a particular environment, the increase in insurance premiums associated with a particular incident which occurs while performing a particular activity or taking place in a particular environment, and/or the like. Non-limiting examples of performance metrics associated with particular activities and/or with particular environments include: a performance rate while performing particular activity or while operating in a particular environment, an error rate while performing particular activity or operating in a particular environment performance rates and/or the like. As used herein, rates may be but need not be strictly temporal. For example, error rates while performing a particular activity may include rates along the lines of: percentage of missed threat objects while performing baggage security screening, number of undetected errors per device examined in an assembly line quality control task; and/or the like.

The terms "fatigue level" and "fatigue state" are used interchangeably throughout the following discussion to refer to an overall level of fatigue of one or more individuals. It is understood that fatigue is inversely related to alertness. That is, when the fatigue level of an individual is higher, his or her alertness level is lower and vice versa. Consequently, the terms alertness level and alertness state may also be used interchangeably with fatigue level and/or fatigue state. Other types of neurobehavioral performance such as "sleepiness", "alertness", "tiredness", "cognitive performance", and/or "cognitive throughput" may be conceptually distinguished from "fatigue" in some contexts. As used herein, however, the terms "fatigue level" and "fatigue state" should be understood in the broader sense to include indicators of these types of neurobehavioral performance. Systems and methods according to particular embodiments may be used to determine (e.g. to estimate and/or to measure) fatigue levels of an individual for the purpose of generating one or more CPMs therefrom. For the sake of brevity, this description may refer to one or more individuals in the singular ("individual") or the plural ("individuals") and/or using one or more synonymous terms (e.g., "subject" and/or the like) interchangeably. An administrative user of the system may be referred to as a "user" or "system user." In some cases the user and individual may be one person.

Embodiments of the invention may make use of one or more techniques for measuring or testing an individual's alertness or fatigue. A variety of such fatigue/alertness measurement/testing techniques (referred to hereinafter as fatigue-measurement techniques) are known. Particular embodiments of the invention are sufficiently adaptable to utilize many (if not all) of these known fatigue-measurement techniques. Non-limiting and non-mutually exclusive examples of suitable fatigue-measurement techniques which may be used in various embodiments of the invention include testing techniques which use: (i) objective reaction-time tasks and cognitive tasks such as the Psychomotor Vigilance Task (PVT) or variations thereof (Dinges, D. F. and Powell, J. W. "Microcomputer analyses of performance on a portable, simple visual RT task during sustained operations." Behavior Research Methods, Instruments, & Computers 17(6): 652-655, 1985) and/or a so-called digit symbol substitution test; (ii) subjective alertness, sleepiness, or fatigue measures based on questionnaires or scales such as the Stanford Sleepiness Scale, the Epworth Sleepiness Scale (Jons, M. W., "A new method for measuring daytime sleepiness—the Epworth sleepiness scale." Sleep 14 (6): 54-545, 1991), and the Karolinska Sleepiness Scale (Åkerstedt, T. and Gillberg, M. "Subjective and objective sleepiness in the active individual." International Journal of Neuroscience 52: 29-37, 1990); (iii) EEG measures and sleep-onset-tests including the the Karolinska drowsiness test (Åkerstedt, T. and Gillberg, M. "Subjective and objective sleepiness in the active individual." International Journal of Neuroscience 52: 29-37, 1990), Multiple Sleep Latency Test (MSLT) (Carskadon, M. W. et al., "Guidelines for the multiple sleep latency test—A standard measure of sleepiness." Sleep 9 (4): 519-524, 1986) and the Maintenance of Wakefulness Test (MWT) (Mitler, M. M., Gujavarty, K. S. and Browman, C. P., "Maintenance of Wakefulness Test: A polysomnographic technique for evaluating treatment efficacy in patients with excessive somnolence." Electroencephalography and Clinical Neurophysiology 53:658-661, 1982); (iv) physiological measures such as tests based on blood pressure and heart rate changes, and tests relying on pupillography and/or electrodermal activity (Canisius, S. and Penzel, T., "Vigilance monitoring—review and practical aspects." Biomedizinische Technik 52(1): 77-82., 2007); (v) embedded performance measures such as devices that are used to measure a driver's performance in tracking the lane marker on the road (U.S. Pat. No. 6,894,606 (Forbes et al.)); and (vi) simulators that provide a virtual environment to measure specific task proficiency such as commercial airline flight simulators (Neri, D. F., Oyung, R. L., et al., "Controlled breaks as a fatigue countermeasure on the flight deck." Aviation Space and Environmental Medicine 73(7): 654-664, 2002); and/or (vii) the like. Particular embodiments of the invention may make use of any one or more of the fatigue-measurement techniques described in the aforementioned references or various combinations and/or equivalents thereof. All of the publications referred to in this paragraph are hereby incorporated by reference herein.

Embodiments of the invention may make use of one or more techniques for modeling an individual's alertness or fatigue. A variety of such fatigue/alertness modeling techniques (referred to hereinafter as fatigue-modeling techniques) are known. Particular embodiments of the invention are sufficiently adaptable to utilize many (if not all) of these known fatigue-modeling techniques. In one particular embodiment, human fatigue is modeled using the so called "two-process model" of sleep regulation developed by Borbely (Borbély, A., Achermann, P., "Sleep Homeostatis and Models of Sleep Regulation." Jounal of Biological Rhythms 14 (6): 559-568, 1999). This model posits the existence of two primary regulatory mechanisms: (i) a sleep/wake-related mechanism that builds up exponentially during the time that subject is awake and declines exponentially during the time that subject is asleep, called the "homeostatic process" or "process S"; and (ii) an oscillatory mechanism with a period of approximately 24 hours (with associated inter-individual variation and often displaying higher-order harmonic intra-individual variation as well), called the "circadian process" or "process C". Without wishing to be bound by theory, the circadian process has been demonstrated to be orchestrated by the suprachiasmatic nuclei of the hypothalamus. The neurobiology of the homeostatic process is only partially known and may involve multiple neuroanatomical structures. The reference cited in this paragraph is hereby incorporated herein by reference.

Fatigue-modeling techniques used by various embodiments of the invention are not limited to the two process model however. Any suitable fatigue-modeling technique may be used in accordance with particular embodiments. Non-limiting and non-mutually exclusive examples of such fatigue-modeling techniques can readily be found within the prior art. One such fatigue modeling technique is described in U.S. Pat. No. 6,530,884 issued to Balkin et al. on Mar. 11, 2003 for a "Method and System for Predicting Human Cognitive Performance" (the "Balkin '884 Patent" hereinafter). The Balkin '884 Patent discloses a fatigue-modeling technique that predicts cognitive performance of an individual based upon, inter alia, sleep history, and the individual's activities. The underlying mathematical model to the fatigue-modeling technique disclosed in the Balkin '884 Patent uses wake functions, sleep functions, and transition functions in combination with sleep history to gauge the cognitive performance of the individual (see Balkin '884 Patent, FIG. 2). Additional patents utilizing the Balkin '884 Patent's mathematical model include the following: U.S. Pat. No. 6,553,252 to Balkin et al. issued Apr. 22, 2003, for a "Method and System for Predicting Human Cognitive Performance;" U.S. Pat. No. 6,740,032 (also) to Balkin et al. issued May 25, 2004, for a "Method and System for Predicting Human Cognitive Performance;" and U.S. Pat. No. 6.743,167 (also) to Balkin et al., issued Jun. 1, 2004, for a "Method and System for Predicting Human Cognitive Performance Using Data from an Actigraph."

Another non-limiting example of a fatigue-modeling technique is disclosed in U.S. Pat. No. 7,192,401 issued to Sallasti et al. on Mar. 20, 2007, for a "Method for Monitoring Accumulated Body Fatigue for Determining Recovery During Exercise or Activity" (the "Sallasti Patent" hereinafter). The Sallasti Patent discloses fatigue-modeling techniques that model human fatigue during and after exercise by employing a piecewise function that accepts as multiple inputs the subject's body-fatigue index and his or her exercise intensity (see Sallasti Patent, FIG. 5). The patent documents cited in this and the preceding paragraph are hereby incorporated herein by reference.

Furthermore, there is knowledge within the prior art of methods for predicting an individual's fatigue level using one of the above-referenced fatigue-modeling techniques without recalculating the individual's predicted fatigue levels from all prior obtained state and trait variable data. It is possible using Bayesian prediction techniques to update the output of prior fatigue-modeling techniques (or, in some cases, prior fatigue-measurement techniques) using only newly added trait or state variable data. One such method, which uses Bayesian prediction methods, is described within PCT publication WO 2009/052633 (see also U.S. Published patent application Ser.

No. 12/739,653), entitled "Systems and Methods for Individualized Alertness Predictions," C. Mott et al., which is hereby incorporated herein by reference.

FIG. 1A is a flowchart illustrating a method 100 for generating one or more contextual performance metrics (CPMs) according to a particular embodiment. Method 100 may be practiced in connection with an individual or subject (not shown) who is being evaluated. Method 100 may be implemented or administered by an administrative person (not shown), who may be referred to herein as a user. Method 100 begins with the optional block 101 of receiving, generating and/or otherwise obtaining one or more future activity schedules or future activity scheduling scenarios for the individual. Method 100 then proceeds to block 102, which involves determining (e.g. measuring and/or estimating) the individual's initial fatigue level. The block 102 initial fatigue level may correspond to the current fatigue level of the individual or to a fatigue level of the individual at the beginning of a particular interval of interest. Block 102 may involve the use of one or more fatigue-measurement techniques and/or one or more fatigue-modeling techniques. Method 100 then proceeds to optional block 103 which involves predicting the individual's fatigue level at one or more additional times during the time interval of interest. The block 103 time interval of interest may correspond to a work shift, an expected time interval for some other activity associated with fatigue risk, an expected interval for the individual to be in an environment associated with fatigue risk and/or the like. Block 103 may involve using one or more fatigue-modeling techniques. Block 103 may use, as input, the future activity scheduling data obtained in block 101. In block 104, the block 102 and/or block 103 fatigue levels are transformed into one or more contextual performance metrics (CPMs) readily understandable by non-experts of fatigue science. The block 104 CPMs are output in block 107. Each of the method 100 blocks is described in greater detail below.

Optional block 101 comprises receiving, generating and/or otherwise obtaining input data and/or schedule data relating to the individual which may be used in subsequent blocks of method 100. Block 101 schedule data may include one or more activity schedules for the individual in a time interval of interest (e.g. a future time interval) or one or more hypothetical future activity scheduling scenarios for evaluation (e.g. multiple scheduling options for a given work shift). The block 101 schedule data may include, by way of non-limiting example, expected start and stop times of: sleep in the time interval; performing one or more particular activities in the time interval; being in one or more particular environments in the time interval; and/or the like. In an example application, where method 100 is being applied in connection with a workplace scenario, the block 101 schedule data may include details such as, without limitation, start and stop times associated with: work; sleep; particular activities such as specific work assignments, job functions, job roles, job titles, work with particular machinery, work with high physical and/or mental requirements; particular environments, such as work environments, commuting environments; and/or the like.

In addition to schedule data, block 101 may also involve receiving, generating and/or otherwise obtaining other forms of input data or input parameters which may be useful for the operation of the methods described herein. Such block 101 input data may originate from the user (e.g. the person administrating the application of method 100), from the individual (e.g. the subject of the application of method 100) or from some external system (not shown). Some non-limiting examples of such input data/parameters are described in more detail below. The block 101 schedule data and/or input data/ parameters may be used to provide optional inputs into the fatigue models used in block 103 and optionally in block 102 and to the creation and application of transforms in block 104. In some circumstances, the block 101 schedule data and/or input data may not be necessary.

In some implementations, block 101 may involve receiving, generating and/or otherwise obtaining a set of hypothetical future scheduling scenarios. Method 100 may then be applied to each hypothetical scheduling scenario to generate a plurality of results (e.g. a plurality of CPMs) for evaluation. Such results may be presented to the user, allowing the user to evaluate comparative CPMs associated with the one or more hypothetical scheduling scenarios. In some embodiments, block 101 may involve receiving, generating or otherwise obtaining a baseline or default future activity schedule which may be used for comparative purposes. In some cases, such a baseline future activity schedule may comprise a continuous wakefulness period extending from the block 102 initial time through to a prediction horizon (e.g. up to an end of the block 103 time interval of interest).

Block 102 involves determining (e.g. measuring and/or estimating) an initial fatigue level for the individual. The block 102 initial fatigue level may correspond to the individual's current fatigue level or to the individual's fatigue level at some other initial time (e.g. at the beginning of a particular time interval of interest). Block 102 may involve the use of one or more fatigue-measurement techniques and/or one or more fatigue-modeling techniques, such as any of those described above. Determining the block 102 fatigue level may involve collecting and/or measuring input data from, or on behalf of, the individual. Such block 102 input data may include data related to the individual's sleeping history, historical sleeping patterns, activity (e.g. work) history and/or activity patterns. Such block 102 input data may be obtained, for example, using: test or survey answers; actigraphy data; a sleep log; prior activity (e.g. work) schedule(s); an estimate of sleep-work schedules or patterns, and/or the like. Block 102 may involve analyzing historical sleep data and/or historical activity (e.g. work) data to determine the initial fatigue level. In addition to sleep and activity history, block 102 may involve analyzing available input data to estimate the individual's historical sleep/wake patterns, circadian rhythm patterns and/or the like. In addition to being used for the block 102 initial fatigue level estimates, the block 102 input date and the block 102 output information may form additional input into the block 103 fatigue model described further below.

As discussed above, block 102 may use any one or more suitable fatigue-measurement techniques and/or fatigue modeling techniques (including any of those described above) for determining the initial fatigue level of the individual. At the conclusion of block 102, method 100 has determined an initial fatigue level of the individual at an initial time which may comprise a current time and/or a time at the beginning of a fatigue interval of interest. This block 102 fatigue level may be used in the remainder of method 100 (e.g. as an input to the block 103 fatigue model). Despite possibly being determined using one or more fatigue-measurement techniques, the block 102 fatigue level may be referred to herein as a model-predicted fatigue level.

Method 100 continues in optional block 103 which involves using one or more fatigue-modeling techniques together with the individual's block 102 initial fatigue level to predict or estimate the individual's fatigue level at one or more future times corresponding to a time interval of interest. In addition to the individual's block 102 fatigue level, the block 103 fatigue-modeling technique may make use of available optional data—such as block 101 schedule data, external factor data (e.g. intake of stimulants), and/or the like. The block 103 fatigue level prediction may be made using any one or more suitable fatigue-modeling techniques, including those described above. In implementations where periodic fatigue estimation is performed on one or more individuals treated separately, block 103 may use individualized fatigue models. By way of non-limiting example, such individualized models may make use of different trait variables corresponding to different individuals. Otherwise, block 103 may use fatigue models geared to specific populations or the overall population at large. By way of non-limiting example, such population-based fatigue models may use trait variables which comprise mean values or probability distribution functions which represent statistical information based on the population of interest. The optional block 103 fatigue level prediction may be made for one or more points in time corresponding to a time interval of interest. At the conclusion of block 103, method 100 has generated an initial model-predicted fatigue level for the individual (in block 102) and optionally one or more model-predicted fatigue levels for the individual at one or more future time points (in block 103).

Method 100 then proceeds to block 104, which involves transforming the block 102, 103 model-predicted fatigue levels (which typically comprise some numerical score or array of scores) into one or more easy-to-interpret contextual performance metrics (CPMs). The block 104 transformation may involve using information (e.g. one or more records) from an historical fatigue database (e.g., historical fatigue database 514 of FIG. 5). The CPMs generated in block 104 may comprise output metrics specific to a particular context which may include one or more of: incident or accident-related metrics associated with particular activities and/or with particular environments; performance metrics associated with particular activities and/or with particular environments; and/or the like.

The block 104 CPMs may include incident related metrics associated with particular activities and/or environments. A non-limiting example of an incident-related metric associated with a particular activity includes an injury severity metric associated with a particular incident (e.g. a vehicular accident) which occurs while performing the particular activity (e.g. driving a truck). A non-limiting example of an incident-related metric associated with a particular environment includes an injury severity metric associated with a particular incident (e.g. a vehicular accident) which occurs in a particular environment (e.g. on a particular stretch of road). The block 104 CPMs may include performance metrics associated with particular activities and/or environments. A non-limiting example of a performance metric associated with a particular activity includes a rate of throughput while performing a particular activity (e.g. making widgets). A non-limiting example of a performance metric associated with a particular environment includes a rate of throughput while operating in a particular environment (e.g. on the graveyard shift).

Figure 1B:
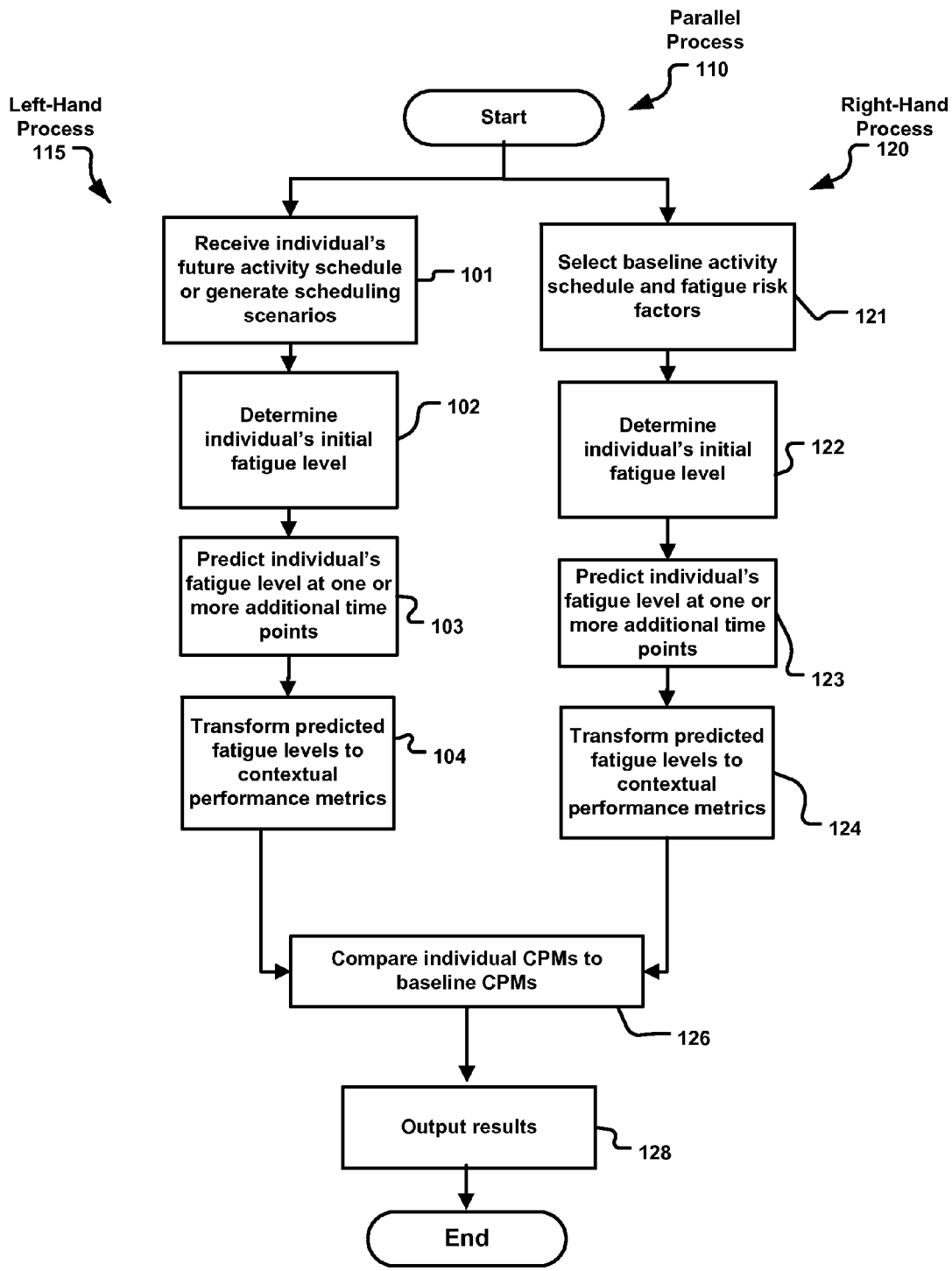
FIG. 1B is a flowchart showing a method for generating comparative contextual performance metrics based on a comparison of CPMs generated for an individual for hypothetical future activity schedules to CPMs generated for a future activity schedule baseline according to a particular embodiment.
Figure 2:
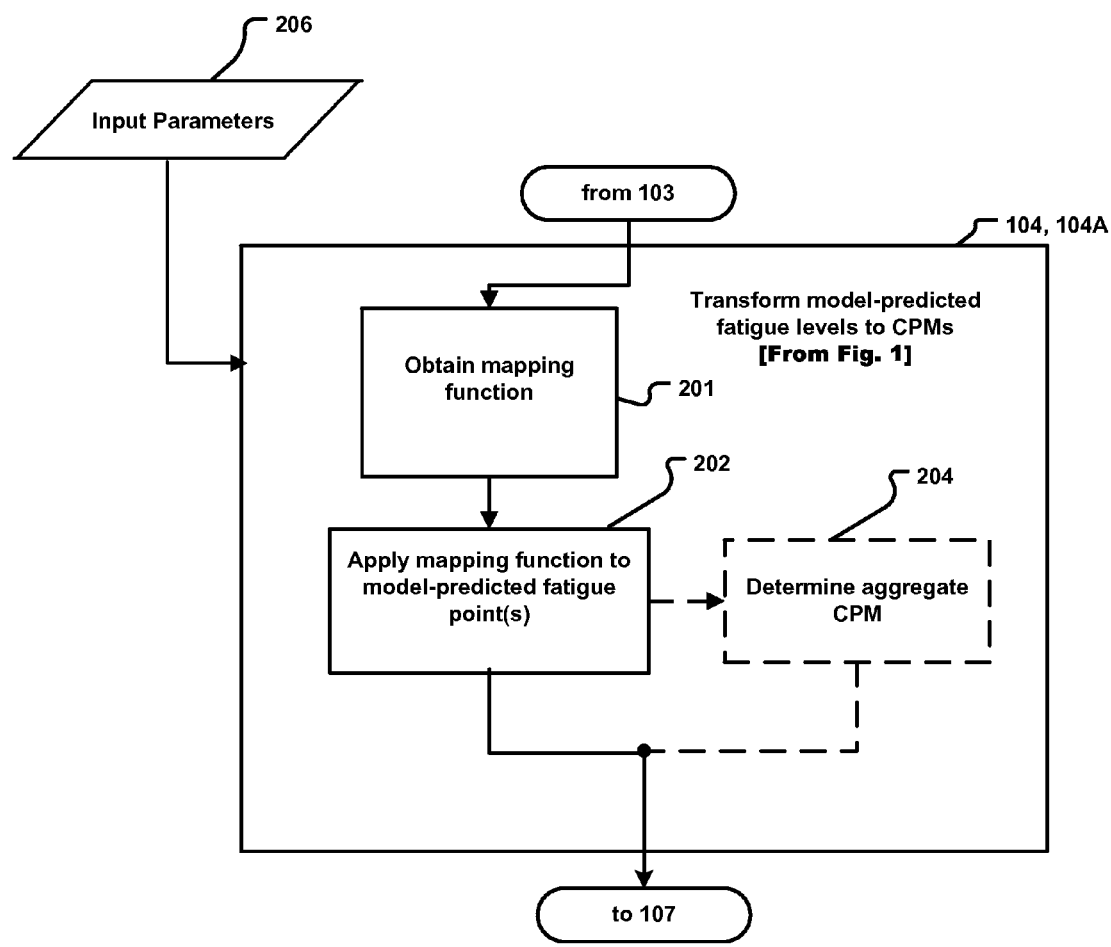
FIG. 2 is a flowchart showing a method for transforming model-predicted fatigue levels into CPMs suitable for use as part of the methods of FIGS. 1A and 1B according to a particular embodiment.

FIG. 2 provides a flowchart of a method 104A which may be used for transforming model-predicted fatigue levels (e.g. the outputs of blocks 102, 103) into CPMs according to a particular embodiment. Method 104 of FIG. 2 may be suitable for use in block 104 of method 100. In the illustrated embodiment, method 104A commences in block 201, which involves obtaining a mapping function which translates or otherwise maps model-predicted fatigue levels (e.g. the model-predicted fatigue levels determined in blocks 102, 103 (FIG. 1) into CPMs. The block 201 mapping function may generally take any suitable format, such as, by way of non-limiting example: a piecewise or discrete function, a continuous function, a lookup table, or any other similar mathematical tool capable of establishing a correspondence between model-predicted fatigue levels (as input) and CPMs (as output). The block 201 process of obtaining a mapping function may involve, without limitation: creating a mapping function based on information (e.g. one or more records) from an historical fatigue database; and/or selecting a mapping function from among one or more existing mapping functions previously created (e.g. in previous iteration(s) of method 201) based on information from an historical fatigue database.

Figure 6A:
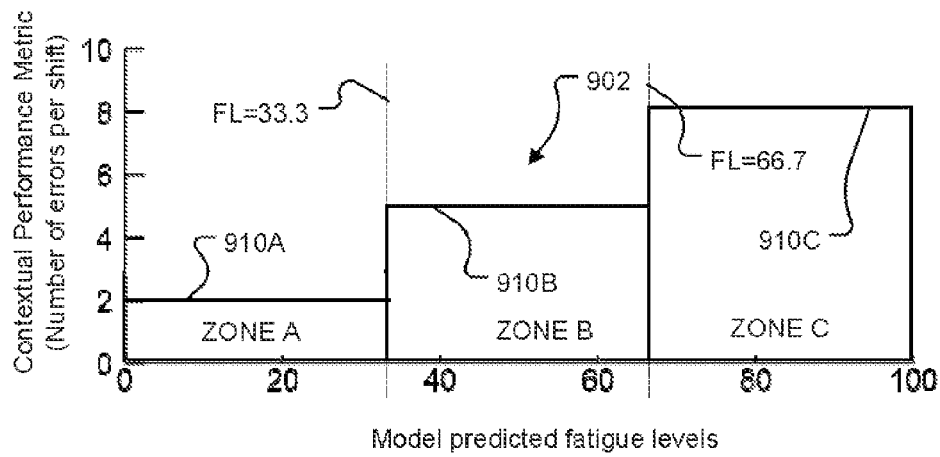
FIG. 6A shows an exemplary discrete transform function which maps model-predicted fatigue levels to CMPs according to a particular embodiment where the discrete binning zones are assigned based on fatigue levels.

FIG. 6A shows an exemplary transform function 902 which maps model-predicted fatigue levels (shown on the x-axis of FIG. 6A) to CPMs (shown on the y-axis of FIG. 6A) according to a particular embodiment. Transform function 902 is exemplary of a type of transform function which may be obtained as a part of block 201. In the illustrated example transform function 902, the model-predicted fatigue level is expressed as a numerical value between 0 and 100, and the CPM represents a number of errors in a work shift. Transform function 902 is an example of a discrete transform function, which includes a finite number (e.g. 3 in the illustrated embodiment) of discrete bins or zones, referred to zone A, zone B and zone C. Each of the function 902 zones maps a plurality of model-predicted fatigue levels to a corresponding CPM value. For example, zone A maps model-predicted fatigue levels in a range of 0 to 33 onto a CMP metric of 2 errors/shift, zone B maps model-predicted fatigue levels in a range of 33 to 67 onto a CMP metric of 5 errors/shift, and zone C maps model-predicted fatigue levels in a range of 67 to 100 onto a CMP metric of 8 errors/shift. It will be appreciated that the number of bins or zones in a discrete mapping function may vary, if a finer degree of precision is desired.

Figure 6B:
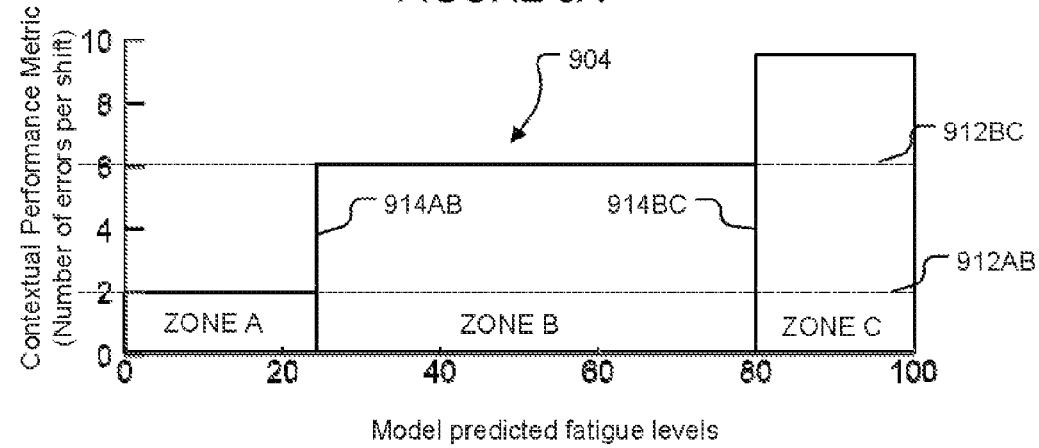
FIG. 6B shows an exemplary discrete transform function which maps model-predicted fatigue levels to CPMs according to a particular embodiment where the discrete binning zones are assigned based on CPM levels.
Figure 6C:
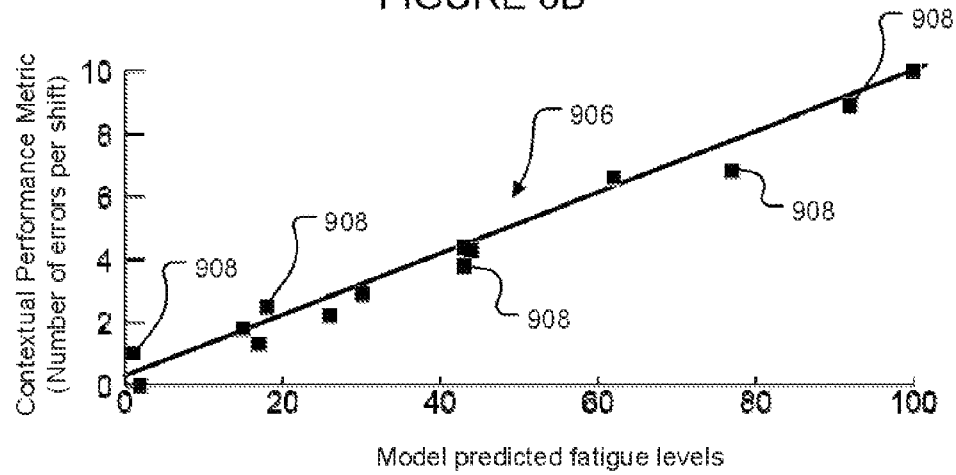
FIG. 6C shows an exemplary continuous mapping function which maps model predicted fatigue levels to CPMs according to a particular embodiment.

FIG. 6C shows another exemplary transform function 906 which maps model-predicted fatigue levels (shown on the x-axis of FIG. 6C) to CPMs (shown on the y-axis of FIG. 6C) according to a particular embodiment. Transform function 906 is exemplary of a type of transform function which may be obtained as a part of block 201. In the illustrated example transform function 906, the model-predicted fatigue level is expressed as a numerical value between 0 and 100, and the CPM represents a number of errors in a work shift. Transform function 906 is an example of a continuous transform function which maps model-predicted fatigue levels to CPMs according to some mathematical function. While transform function 906 may be based on a mathematical function, it is not necessary that transform function 906 be stored or applied as a mathematical function. As discussed above, transform function 906 may be stored or applied in the form of a look-up table. In the illustrated embodiment, transform function 906 is a linear function, although this is not necessary, and transform function 906 may have any suitable mathematical form. Rather than having bins or zones, transform function 906 maps each value of model-predicted fatigue level to a corresponding CPM value according to its underlying mathematical function. It can be seen from transform function 906 that relatively low levels of model-predicted fatigue correspond to relatively low error rates, whereas relatively high levels of model-predicted fatigue correspond to relatively high error rates.

Referring back to FIG. 2, block 201 may involve selecting a mapping function from among previously created mapping functions. In such cases, mapping functions 902, 906 described above represent exemplary mapping functions which may be selected in block 201. Block 201 may, in some instances, involve creating a mapping function. The creation of a mapping function in block 201 may be based on information (e.g. one or more records) from an historical fatigue database. In particular embodiments, the records of an historical fatigue database comprise the following fields:

(i) one or more "activity type" fields which classify the record according to activity type. Non-limiting examples of activity types which may populate a record include: operating a motor vehicle, making widgets, testing widgets, performing a military operation and/or the like. Activity types of a particular record may comprise subclasses of one another. For example, activity types corresponding to one record may include: operating a motor vehicle, operating an airplane, operating a Boeing 767 and/or the like. It is not necessary that a record of the historical fatigue database include an activity type. For example, in some instances, records that include one or more environment types need not include an activity type.

(ii) one or more "environment type" fields which classify the record according to environment type. Non-limiting examples of environment types which may populate a record include: a driver/pilot seat of a motor vehicle, a widget-making factory X, a particular stretch of highway, at night, a particular geographical region and/or the like. Like activity types, environment types of a particular record may comprise subclasses of one another. For example, environment types corresponding to one record may include: a highway, a divided highway, on Interstate Highway 5 and/or the like. It is not necessary that a record of the historical fatigue database include an environment type. For example, in some instances, records which include one or more activity types need not include an environment type.

(iii) a fatigue level. This fatigue level may comprise a model-predicted fatigue level of one or more individuals whose data was used to populate the historical fatigue database and who were associated in some way with the activity type(s) and/or the environment type(s) of the record. The fatigue level may comprise, or may be based upon, a fatigue level estimated using a fatigue-modeling technique and/or measured using a fatigue-measurement technique, like any of those discussed above.

(iv) one or more contextual performance metrics (CPMs) which represent fatigue-related metrics specific to a particular context (e.g. to the activity types and/or the environment types associated with the record) and which may be measured or otherwise obtained during population of the historical fatigue database. CPMs may include one or more of: incident or accident-related metrics associated with the record's activity type(s)/environment type(s), performance metrics associated with the record's activity type(s)/environment type(s), and/or the like.

In some embodiments, records of the historical fatigue database may comprise other suitable additional or alternative fields that may be used to create mapping functions. By way of non-limiting example, the record described above includes activity types and/or environment types that are used to classify the record. In general, other types of record-classification criteria may be used. Such record-classification criteria may be specific to specific circumstances or situations. For example, such record-classification criteria may comprise: experience/training level, age, sex, body mass ratio and/or the like corresponding to the person or people used to generate the record.

Figure 3:
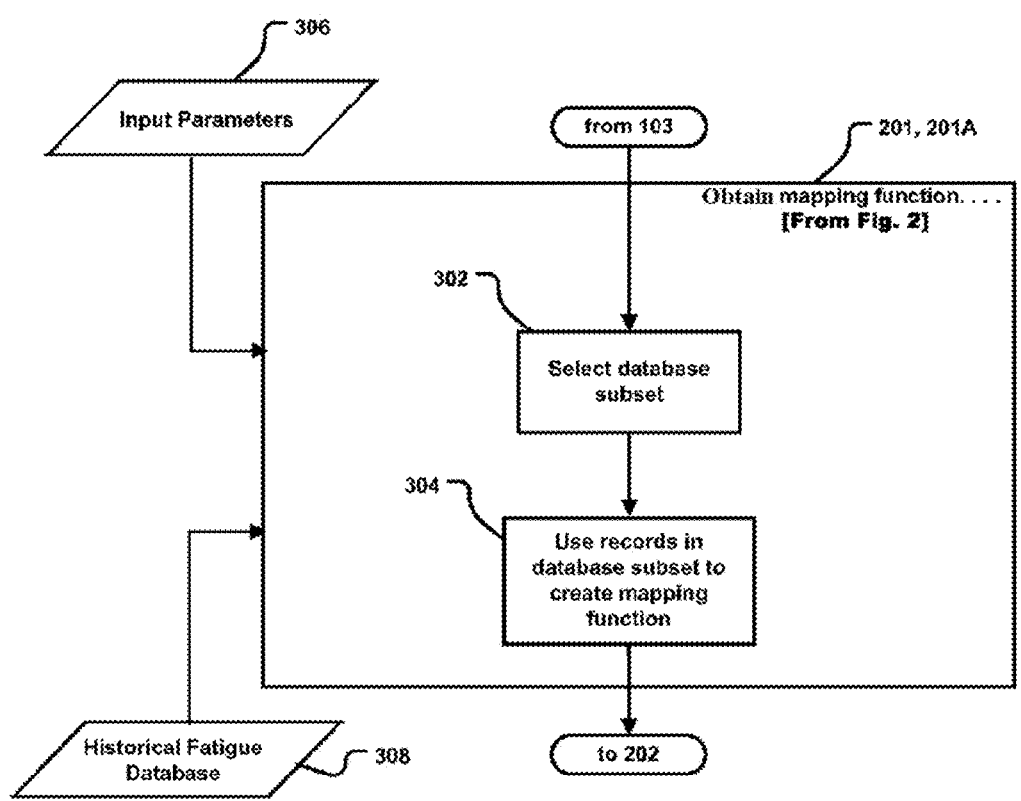
FIG. 3 is a flowchart showing a method for creating a mapping function which may be used to translate one or more model-predicted fatigue levels into CPMs according to a particular embodiment which may be suitable for use as part of the method of FIG. 2.

FIG. 3 is a flowchart showing a method 201A for creating a mapping function which may be suitable for use when block 201 of method 104A (FIG. 2) involves creating a mapping function. Method 201A starts in block 302, which involves selecting a subset of interest from within historical fatigue database 308. The block 302 database subset selection may be based on one or more input parameters 306. Input parameters 306 may originate from the user (e.g. the person administrating the application of method 100 (FIG. 1A)), from the individual (e.g. the subject of the application of method 100), or from some external system, and input parameters 306 may be obtained in block 101, although this is not necessary. Such input parameters 306 may specify one or more activity types and/or environmental types of interest. For example, input parameters 306 may specify that the subset of interest of historical fatigue database 308 corresponds to: the activity type of piloting a fighter jet, both the activity type of piloting a fighter jet and the environment type of at night; a plurality of activity types such as piloting a fighter jet and piloting a F16 fighter jet and/or the like. Where such input parameters 306 are provided, block 302 may involve canvassing the activity types and/or environment types of the records of historical fatigue database 308 and selecting a database subset based on correspondence with the input activity type(s) and/or environment type(s). It will be appreciated that where historical fatigue database 308 comprises different record-classification criteria, such different record-classification criteria may be used in block 302 to select a corresponding database subset.

Once the database subset is selected in block 302, method 201A proceeds to block 304, which involves using the information contained in the block 302 database to create a mapping function. The block 304 mapping function creation may also be based on input parameters 306. Input parameters 306 may specify one or more characteristics of the mapping function to be created in block 304. By way of non-limiting example, input parameters 306 may specify that the mapping function to be created should be a discrete mapping function (e.g. like mapping function 902 of FIG. 6A) or a continuous mapping function (e.g. like mapping function 906 of FIG. 6C). As another example, input parameters 306 may specify the type of function to be used for a continuous mapping function (e.g. a linear function, a polynomial function, an exponential function, a Gaussian function and/or the like) or the number of bins/zones in a discrete mapping function.

Input parameters 306 may also specify one or more characteristics of how to create the block 304 mapping function. By way of non-limiting example, input parameters 306 may specify a curve fitting technique (discussed further below) for creating a continuous mapping function or a binning technique (discussed further below) for creating a discrete mapping function.

In some embodiments, block 304 involves creating a continuous mapping function. As discussed above, mapping function 906 of FIG. 6C represents an example of a continuous mapping function. Let us assume, for the purposes of presenting an explanatory example, that the block 302 database subset comprises a number of records, with each record comprising a corresponding fatigue level field and a corresponding CPM field (e.g. errors per shift). Let us assume further that the data points 908 shown on the plot of FIG. 6C represent corresponding pairs of (fatigue level, CPM). Creating a continuous mapping function in block 304 may involve performing a curve-fitting and/or optimization process so as to best match the (fatigue level, CPM) data points 908. In the illustrated embodiment, where the curve being fit to data points 908 is a linear curve of the form $CPM=aFL+b$ where CPM is the CPM output value, FL is the fatigue level, the block 304 curve-fitting process may involve selecting the curve parameters a and b by minimizing some cost function or the like. It will be appreciated that where the mapping function is expected to have a form (e.g. a function type other than linear), the mapping function may be characterized by different parameters, which may be determined using suitable curve-fitting techniques. There are a wide variety of curve fitting techniques known to those skilled in the art which may be suitable for use to create a mapping function in block 304.

In some embodiments, block 304 involves creating a discrete mapping function. As discussed above, mapping function 902 of FIG. 6A represents an example of a discrete mapping function. Let us assume, again, that the data points 908 shown on the plot of FIG. 6C represent corresponding pairs of (fatigue level, CPM) contained in the block 302 database subset. In the case of the illustrated embodiment of FIG. 6A, input parameters 306 may specify that the number of bins/zones to be used in mapping function 902 is 3 and that the bins/zones are to have equal ranges in fatigue space (e.g. zone A corresponds to fatigue levels 0-33.3; zone B corresponds to fatigue levels 33.4-66.7 and zone C corresponds to fatigue levels 66.8-100). In such cases, data points 908 may be classified into their respective bins/zones according to this rule. The data points 908 within each respective zone may then be combined in some fashion to create a CPM output value 910A, 910B, 910C for their respective bin/zone. The method for combining the data points 908 within a particular zone to arrive at a corresponding CPM value 910A, 910B, 910C may be specified by input parameters 306. In the illustrated embodiment, the method for combining the data points 908 within a particular zone may involve averaging the CPM values of the individual data points 908 to generate a CPM value 910A, 910B, 910C corresponding to the particular zone. For example, in the illustrated embodiment of FIG. 6A with data points 908 of FIG. 6C, the average CPM value of the data points 908 in zone A is CPM≈3, the average CPM value of the data points 908 in zone B is CPM≈5 and the average CPM value of the data points in zone C is CPM≈8. It will be appreciated that averaging is not the only technique for combining the CPM values 908 in a particular zone to arrive at a CPM value 910A, 910B, 910C for the zone. In other embodiments, other techniques may be used for such combination. By way of non-limiting example, it may be desirable to weight certain data points from within the particular zone differently than others based, for example, upon the proximity of their fatigue levels to a zone boundary.

FIG. 6B shows a mapping function 904 which represents another example of a discrete mapping function which may be created in block 304 (FIG. 3). Discrete mapping function 904 differs from discrete mapping function 902 in that input parameters 306 do not require the bins/zones of mapping function 904 to be evenly spaced in fatigue-level space. Instead, input parameters 306 may specify that the bins/zones of mapping function 904 are to be selected based on CPM values. In the case of the illustrated embodiment of FIG. 6B, input parameters 306 may specify two zone boundaries 912AB, 912BC in CPM space which may be used to create a discrete transform function having three zones (zone A, zone B, zone C). In this illustrated embodiment of FIG. 6B, a first CPM zone boundary 912AB is specified as 2 errors per shift. A corresponding first fatigue level boundary 914AB may then be determined such that the average of the CPMs of data points 908 having fatigue levels in a range between the minimum fatigue level (FL=0) and the first fatigue level boundary 914AB matches the corresponding first CPM zone boundary 912AB. In the illustrated embodiment of FIG. 6B a second CPM zone boundary 912BC is specified as 6 errors per shift.

A corresponding second fatigue level boundary 914BC is then calculated such that the average of the CPMs of data points 908 having fatigue levels in a range between the first fatigue level boundary 914AB and the second fatigue level boundary 914BC matches the second CPM zone boundary 912BC. In the illustrated embodiment of FIG. 6B, the third zone (zone C) is defined as corresponding to fatigue levels ranging between the second fatigue level boundary 914BC and the maximum fatigue level (FL=100). The CPM value for the third zone (zone C) may be determined as an average of the CPM values of data points 908 with fatigue levels in this third zone. It will be appreciated that averaging is not the only technique for combining the CPM values of data points 908 to arrive at the specified CPM boundary values 912AB, 912BC. As with the creation of the discrete mapping function 902 of FIG. 6A, in other embodiments, other techniques may be used for combining CPM values.

In other embodiments, block 304 may use other techniques to create a mapping function between model-predicted fatigue levels and CPM values based on information contained in the records of the block 302 database subset. Suitable input parameters 306 may be solicited and obtained (e.g. from the user, the individual or an external system) for the purposes of facilitating the creation of mapping functions according to such other techniques. At the conclusion of block 304, method 201A returns to block 202 (FIG. 2) with a mapping function which maps model-predicted fatigue levels to CPM values.

Block 202 of method 104A (FIG. 2) involves applying the block 201/method 201A mapping function to the initial model-predicted fatigue levels determined in block 102 (FIG. 1A) and estimated for the time interval of interest in block 103 (FIG. 1A). The output of block 202 comprises one or more CPM values corresponding to the one or more model-predicted fatigue levels at one or more corresponding time points ascertained in blocks 102, 103. The output CPM values of block 202 represent context-specific and easy-to-understand metrics which correspond to the individual whose model-predicted fatigue levels are obtained in blocks 102, 103 and which correspond to the time points in block 103 time interval of interest. For example, where the CPM under consideration is the number of errors per shift (as is the case for example in the mapping functions of FIGS. 6A, 6B and 6C), the block 202 output may comprise a predicted number of errors/shift for the individual for each of a plurality of time points (e.g. one per shift) for a time interval of interest (e.g. one week).

Figure 7A:
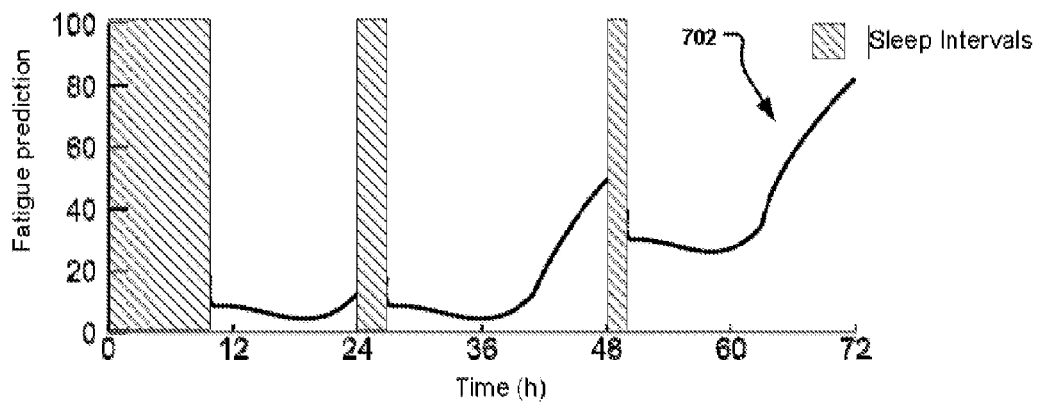
FIGS. 7A, 7B and 7C are plots which respectively depict exemplary model-predicted fatigue levels, an exemplary CPM output based on the FIG. 6A discrete transform function and an exemplary CPM output based on the FIG. 6C continuous transform function for a particular sleep pattern according to a particular embodiment.
Figure 7B:
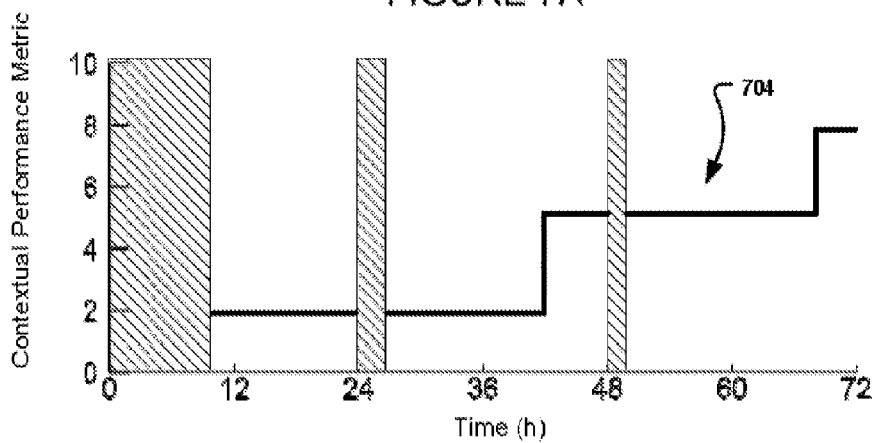
Figure 7C:
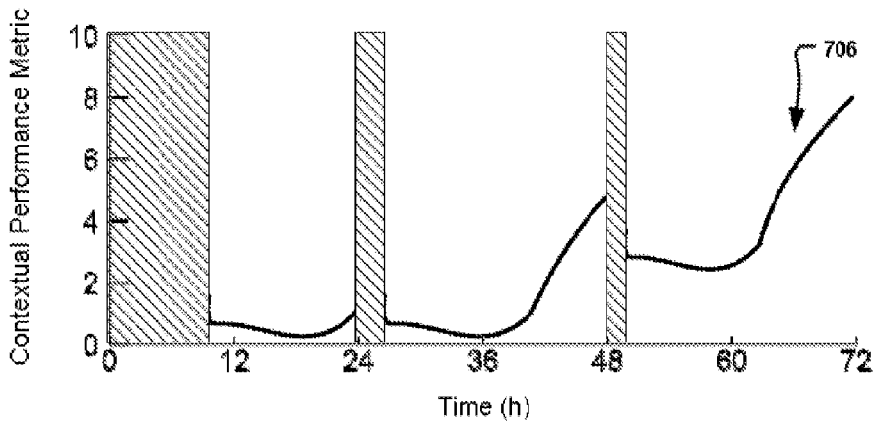

FIGS. 7A, 7B and 7C are temporal plots of exemplary model-predicted fatigue levels 702, an exemplary CPM output 704 (based on the FIG. 6A discrete mapping function) and an exemplary CPM output 706 (based on the FIG. 6C continuous mapping function) for a particular sleep pattern. The plot 702 model-predicted fatigue levels may be representative of fatigue levels determined in blocks 102, 103 for the illustrated sleep pattern. The CPM outputs 704, 706 of FIGS. 7B and 7C may represent the output of block 202 for the FIG. 6A and FIG. 6C discrete and continuous mapping functions, respectively. The particular CPM metric in plots 704, 706 may represent a number of errors/shift, for example, so that a high CPM is generally undesirable.

A number of observations can be made from FIGS. 7A, 7B and 7C. Firstly, it can be observed from plot 702 that the model-predicted fatigue level decreases after a period of sleep, increases after being awake for a period of time, and increases more dramatically after a period of insufficient sleep. Plots 704 (FIG. 7B) and 706 (FIG. 7C) both show that as the model-predicted fatigue level increases, the CPM (number of errors per shift) also increases, which is what one might expect. Plot 704 shows that for the discrete mapping function, the CPM has the zone A level of CPM=2 until the time 42 hours and then jumps to the zone B level of CPM=5 before jumping to the zone C level of CPM=8 at a time around 68 hours. Plot 706 shows that for the continuous mapping function, the CPM level varies continuously while the subject is awake and only exhibits discontinuities when across sleep intervals. Where the continuous mapping function is linear (as is the case for the FIG. 6C mapping function and the corresponding plot 706 of FIG. 7C), the CPM output of plot 706 has a shape that mirrors that of the model-based fatigue estimate of plot 702.

Figure 7D:
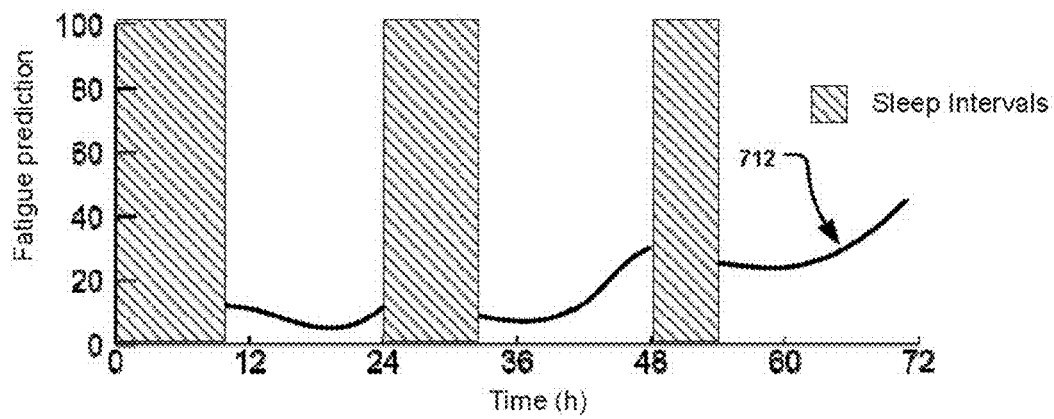
FIGS. 7D, 7E and 7F are plots which respectively depict exemplary model-predicted fatigue levels, an exemplary CPM output based on the FIG. 6A discrete transform function and an exemplary CPM output based on the FIG. 6C continuous transform function for a different particular sleep pattern according to a particular embodiment.
Figure 7E:
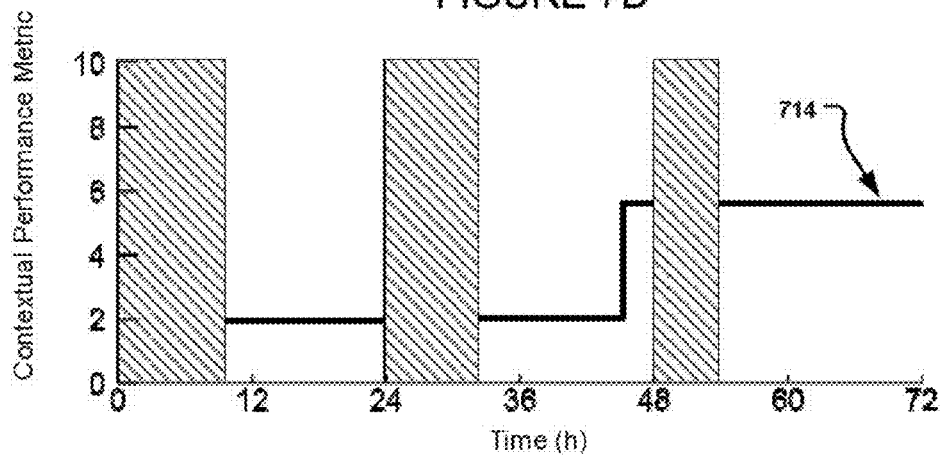
Figure 7F:
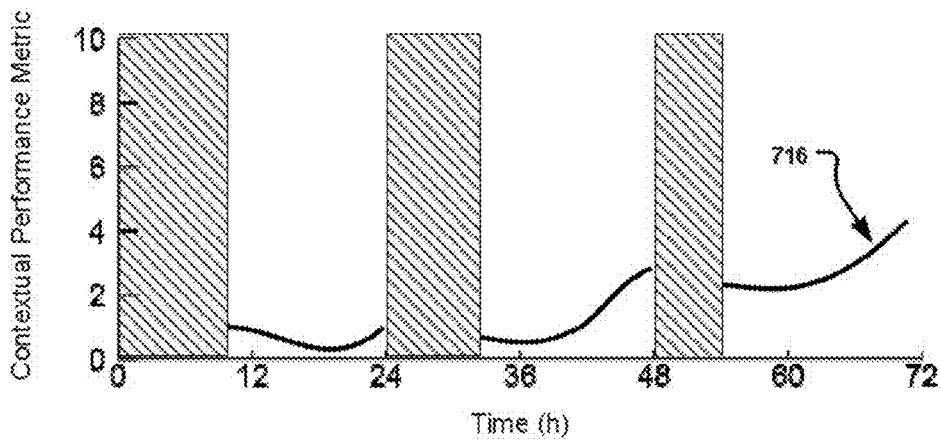

FIGS. 7D, 7E and 7F are temporal plots of exemplary model-predicted fatigue levels 712, an exemplary CPM output 714 (based on the FIG. 6A discrete mapping function) and an exemplary CPM output 716 (based on the FIG. 6C continuous mapping function) for a different sleep pattern. More particularly, the sleep pattern in FIGS. 7D, 7E, 7F involves more sleep than that of FIGS. 7A, 7B, 7C. The consequence of this extra sleep is that the individual's model-predicted fatigue levels and CPM values stay lower. In the particular case of the discrete mapping function (FIG. 7E), the individual's model-predicted fatigue level never reaches a state where the mapping function jumps to the zone C level of CPM=8.

Method 104A (FIG. 2) may optionally include block 204, which determines one or more aggregate CPM values by combining a plurality of the CPM values output from block 202 which corresponding to different time points. Block 204 may comprise any suitable technique for combining two or more block 202 CPM values corresponding to different time points. For example, block 204 may comprise determining an average CPM value corresponding to the block 103 time interval of interest or some subset thereof. Other techniques may be used to combine the block 202 CPM values to generate aggregate CPM values in block 204. By way of non-limiting example, it may be desirable to weight certain block 202 CPM values differently from one another when determining the block 204 aggregate CPM value—e.g. because some time points are considered to be more interesting than others. The aggregate CPM value(s) determined in block 204 and the techniques used for determining such aggregate CPM value(s) may be specified by input parameters 206. Input parameters 206 may originate from the user (e.g. the person administrating the application of method 100 (FIG. 1A)), from the individual (e.g. the subject of the application of method 100) or from some external system.

At its conclusion, method 104A (FIG. 2) outputs one or more block 202 CPM values corresponding to the time points and model-predicted fatigue levels of blocks 102, 103 and optionally outputs one or more block 204 aggregate CPM values and returns to block 107 (FIG. 1A). In block 107, method 100 involves outputting one or more of the block 202 CPM values and, optionally, one or more of the block 204 aggregate CPM values for evaluation by the user (not shown) and/or the individual (not shown). In some embodiments, the block 107 output may be displayed on a suitable local IO device (e.g. a monitor) in a report format that may comprise textual, tabular and/or graphical elements. In some embodiments, the block 107 output may be additionally or alternatively communicated to a remotely located electronic system (e.g. over a suitably configured communications network). In some embodiments, block 107 may involve additional processing of output CPM data, such as performing statistical analysis of the output CPM data or relating the output CPM data to some other data. For example, if the output CPM data represents a number of errors per shift, it may be related to other data such as statistical data relating to the costs associated with errors.

FIG. 1B is a flowchart of a method 110 for generating comparative contextual performance metrics based on a comparison of CPMs generated for an individual for hypothetical future activity schedules to CPMs generated for a future activity schedule baseline according to a particular embodiment. Method 110 includes a "left-hand" process 115 which is similar in many respects to method 100 described above, and similar reference numerals are used to denote similar features. For example, left-hand process 115 may involve: i) obtaining one or more hypothetical future activity schedules in block 101, ii) determining an individual's initial model-predicted fatigue level in block 102, iii) predicting the individual's model-predicted fatigue level at one or more times during a time period of interest in block 103 based on the block 102 initial fatigue level and the block 101 hypothetical future activity schedules, and iv) transforming these model-predicted fatigue levels into CPMs in block 104. It will be appreciated that the processes of blocks 102, 103, 104 of left-hand process 115 may be performed once for each hypothetical future activity schedule specified in block 101. The block 101 hypothetical future activity schedules may be supplied by suitable input data (not shown), which may originate from the user (e.g. the person administrating the application of method 100 (FIG. 1A)), from the individual (e.g. the subject of the application of method 100), or from some external system. For each of the block 101 hypothetical future activity schedules, at the conclusion of block 104, left-hand process 115 has generated a set of CPM values for the individual corresponding to one or more time points in a time interval of interest assuming that the individual will follow the block 101 hypothetical future activity schedule. Optionally, left-hand process 115 may also use its CPM values to generate one or more aggregate CPM values for each of the block 101 hypothetical future activity schedules in a manner analogous to that described in block 204 above.

Method 110 also includes a "right-hand" process 120 which again is similar to method 100 described above and similar reference numerals are used to denote similar features. Right-hand process 120 differs from method 100 in that block 121 replaces block 101. Rather than obtaining hypothetical future activity schedules, block 121 involves obtaining a single "baseline" future activity schedule to which the block 101 hypothetical future activity schedules may be compared. The block 121 baseline future activity schedule may be supplied by suitable input data. By way of non-limiting example, the block 101 hypothetical future activity schedules may comprises different shift changes for the individual and the block 121 baseline future activity schedule may comprise continuing with the status quo shifts. For example, the status quo shifts (and block 121 baseline future activity schedule) may involve work shifts from 8 AM-4 PM and a suitable corresponding sleep schedule (e.g. 11 PM-7 AM). The hypothetical future activity schedules of block 101 may correspond to a switch to evening shifts (e.g. 4 PM-12 AM) and/or to graveyard shifts (e.g. 12 AM-8 AM) with corresponding suitable sleep schedules.

Right hand process 120 then proceeds through blocks 122, 123, 124 which are respectively analogous to blocks 102, 103, 104 of left-hand process 115, except that the block 121 baseline future activity schedule is used in the place of the block 101 hypothetical future activity schedules. In many instances, for the purposes of comparison, it is useful for the time interval of interest (and the individual time points of interest within that time interval) considered in block 123 of right-hand process 120 to be the same or similar to the time interval of interest (and the individual time points of interest within that time interval) considered in block 103 of left-hand process 115, although this is not necessary. At the conclusion of block 124, right-hand process 120 has generated CPM values corresponding to one or more time points for a time interval of interest wherein it is expected that the individual will follow the block 121 baseline activity schedule. These block 124 CPM values may be referred to as baseline CPMs or baseline CPM values. Optionally, right hand process 120 may also use its baseline CPM values to generate one or more aggregate baseline CPM values in a manner analogous to that described in block 204 above.

After the completion of block 104 in left-hand process 115 for one or more of the block 101 hypothetical future activity schedules and completion of block 124 in right-hand process 120 for the baseline future activity schedule, method 110 proceeds to block 126 which involves comparing the CPM values generated for the hypothetical future activity schedules in block 104 to the baseline CPM values generated for the baseline future activity schedules in block 124. It may be determined from this block 126 comparison that a particular block 101 hypothetical future schedule has one or more features or characteristics (which may be based on corresponding CPMs) that make the hypothetical future schedule more or less desirable than the block 121 baseline future activity schedule. For example, reverting to the shift work example discussed above and assuming that the CPMs being considered in method 110 are metrics indicative of an hourly rate of widget manufacture, the block 126 comparison may lead to the conclusion that the expected widget manufacture throughput may drop off sharply when an individual is changed from the baseline day shift to a hypothetical graveyard shift, but that the expected widget manufacture throughput may not drop off as sharply if the individual is changed from the baseline day shift to a hypothetical shift that starts one hour earlier.

Method 110 may then output its results in block 128—e.g. for evaluation by the user (not shown) and/or the individual (not shown). The results output in block 128 may be analogous to those output in block 107 described above and may include, by way of non-limiting example, outputting block 104 CPM values for different block 101 hypothetical future activity schedules, baseline CPM values determined in block A124 and/or corresponding aggregate CPM values. In some embodiments, the block 128 output may be displayed on a suitable local IO device (e.g. a monitor) in a report format that may comprise textual, tabular and/or graphical elements. In some embodiments, the block 128 output may additionally or alternatively communicated to a remotely located electronic system (e.g. over a suitably configured communications network). In some embodiments, block 128 may involve additional processing of output CPM data, such as performing statistical analysis of the output CPM data or relating the output CPM data to some other data.

Figure 4:
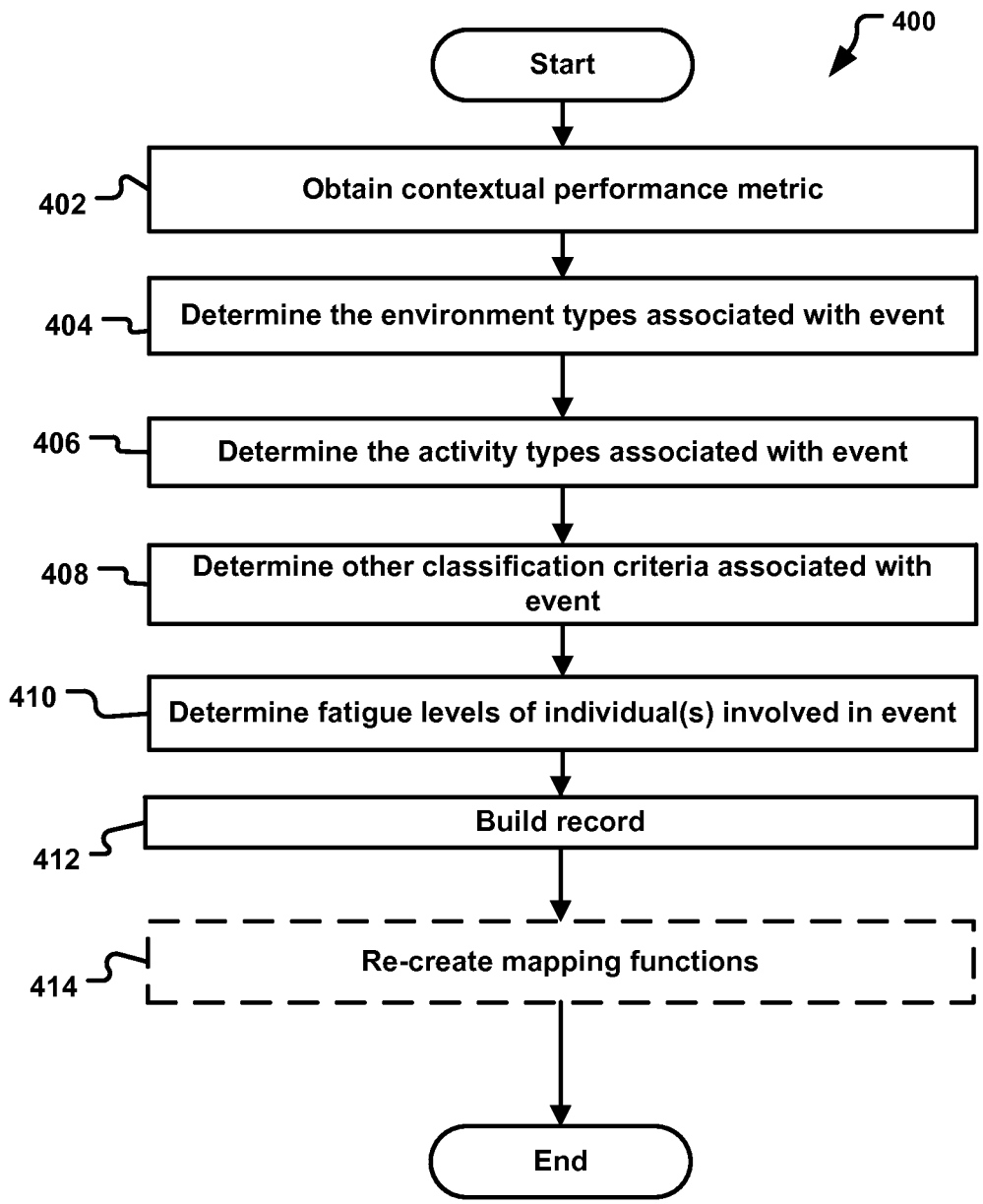
FIG. 4 is a flowchart showing a method for populating an historical fatigue database according to a particular embodiment.

FIG. 4 is a flowchart illustrating a method 400 for populating a record of an historical fatigue database according to a particular embodiment. As described above, to be suitable for use with the methods described herein records of the historical fatigue database may comprise: a CPM field, a fatigue level field and one or more classification fields (which may include, for example, one or more activity fields, one or more environment fields and/or other record-classification fields). Method 400 of the FIG. 4 embodiment assumes that some event of interest has occurred (e.g. an activity of interest or an activity in an environment of interest).

Method 400 begins in block 402, which involves obtaining one or more CPMs associated with the event. Obtaining the block 402 may involve monitoring, measuring, sensing, deriving or otherwise ascertaining information of interest (e.g. contextual metrics) about the method 400 event. In some embodiments, the block 402 CPM can be manually and/or automatically input through an electronic interface, through a networked communication interface, and/or by extracting data from another database or information system. By way of non-limiting example, if an event comprises a work shift in a particular factory, then block 402 may involve measuring assembly line down-time during the shift, the number of widgets manufactured during the shift, the number of widgets that fail inspection during the shift and/or the like. In general, it is possible that more than one CPM can be obtained for a particular event. However, it is generally desirable that each record in the historical fatigue database comprise a single CPM value. Consequently, obtaining multiple CPMs in block 402 may involve generating a corresponding plurality of records by performing corresponding parallel implementations of method 400. For explanatory purposes, the remaining explanation of method 400 assumes that there is only one block 403 CPM value and that only one corresponding record is being generated in method 400.

Method 400 then proceeds to block 404, which involves identifying or otherwise determining environment types associated with the event. The block 404 environment types may be manually and/or automatically input. The block 404 environment types may translate into the environment type fields of the record generated in method 400. The above discussion provides a number of examples of environment types which may be identified in block 404. As discussed above, there may be records in the historical fatigue database that comprise a plurality of environment types or that comprise no environment types. Consequently, block 404 may involve determining that there are a plurality of environment types or that there are no environment types for a particular record. Method 400 then proceeds to block 406, which involves identifying or otherwise determining activity types associated with the event. The block 406 activity types may be manually and/or automatically input. The block 406 activity types may translate into the activity type fields of the record generated in method 400. The above discussion provides a number of examples of activity types which may be identified in block 406. As discussed above, there may be records in the historical fatigue database which comprise a plurality of activity types or which comprise no activity types. Consequently, block 406 may involve determining that there are a plurality of activity types or that there are no activity types for a particular record.

Method 400 then proceeds to block 408, which optionally involves identifying or otherwise determining any other record-classification criteria associated with the event. Such record-classification criteria may translate into corresponding record-classification fields of the record being generated in method 400. The block 408 determination of other record-classification criteria may be similar to the determination of environment types and activity types in blocks 404, 406.

Method 400 then proceeds to block 410 which involves determining (e.g. measuring and/or modeling) the fatigue levels of the individual(s) involved in the event. Block 410 may involve any of the above-discussed fatigue-measurement techniques and/or any of the above-discussed fatigue-modeling techniques. The techniques involved in block 410 may be analogous to those described above for block 102 and/or block 103 (FIG. 1A). For events which are distributed over time, method 400 may involve obtaining a fatigue level for the individual(s) at a certain time relative to the event (e.g. at a beginning of the event, at the end of an event, at specific time intervals during the event and/or the like) or as an aggregate fatigue level reflecting or relative to fatigue levels at multiple times during the event (e.g. average fatigue level at every 5 minutes during event, maximum fatigue level during the event, and/or the like). Where there are multiple individuals associated with an event, block 410 may involve obtaining fatigue levels for each of the multiple individuals and then combining (e.g. by averaging or otherwise) these fatigue levels to obtain a single fatigue level which may be used in the method 400 record. In some embodiments, where there are multiple individuals associated with an event, method 400 may create multiple records, one for each individual. Additional metrics such as the degree of an individual's involvement or contribution to an event may be included in the record for that particular individual. The fatigue level determined in block 410 may be referred to as a model-predicted fatigue level.

Method 400 then proceeds to block 412 which involves building up the record using the block 402 CPM data, any available block 404 environmental type data, any available block 406 activity type data, any available block 408 other classification-criteria and the block 410 model-predicted fatigue level. The block 412 record may then be added to the historical fatigue database. Method 400 may optionally proceed to block 414, which involves recreating mapping functions based on the new information added to the historical fatigue database. The specific mapping functions which may be recreated in block 414 include those which correspond to the block 404 environment types, the block 406 activity types and the block 408 other classification-criteria types of the newly added record. The method of recreating mapping functions in block 414 may be similar to that described above for method 201A (FIG. 3).

Figure 5:
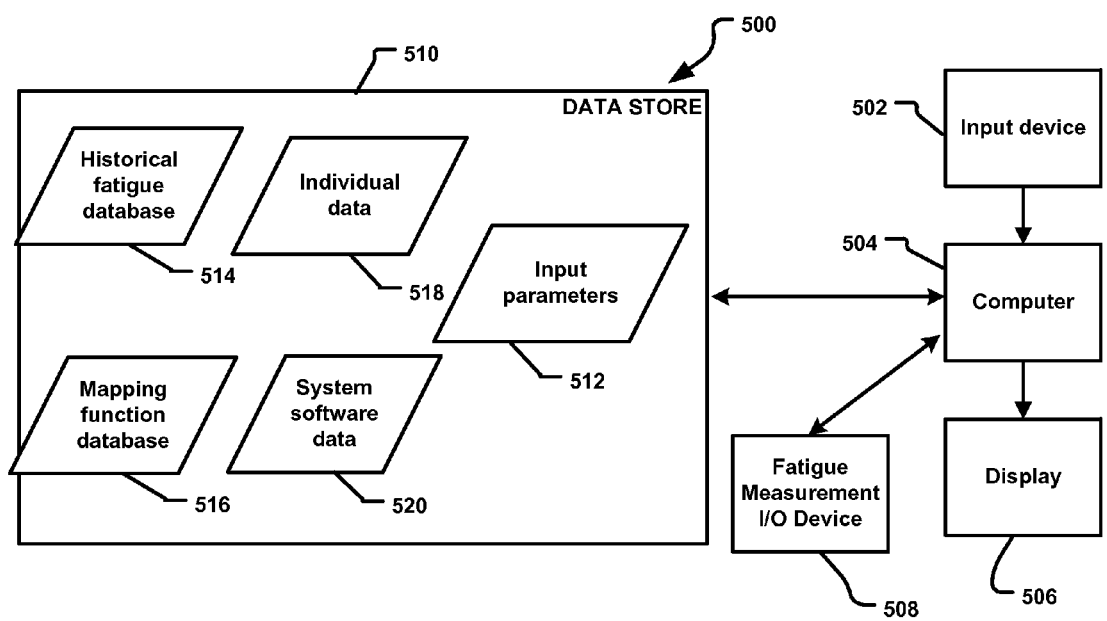
FIG. 5 is a schematic diagram of a system which may be used for implementing the methods described herein according to particular embodiment.

FIG. 5 is a schematic diagram of a system 500 which may be used for implementing some of the methods described herein according to particular embodiments. For brevity, some well understood components of system 500 are not shown in the FIG. 5 schematic illustration, but will be understood by those skilled in the art. System 500 comprises a suitably programmed computer 504 having a suitable input device 502 and a monitor display 506. Input device 502 may comprise any suitable input device capable of interacting with computer 504, including without limitation keyboards, pointing devices, touch screens, and voice input and/or the like. Computer 504 may be configured for network communications with one or more local area networks (LANs) and/or wide area networks (WANs) (not shown). In the illustrated embodiment, system 500 also comprises an optional fatigue measurement I/O device 508 which may be used to measure or sense one or more parameters of an individual which may be indicating of the individual's fatigue level.

Computer 504 of the illustrated embodiment has access (locally or through a network) to data store 510. Data store may store input parameters 512 for the operation of the various methods described above, historical fatigue database 514 comprising historical fatigue records, mapping function database 516 comprising mapping functions which have been previously created, individual data 518 corresponding to the individual to whom the methods are being applied, system software data 520 which may include programs operating on computer 504 and/or the like.

Certain implementations of the invention comprise computers and/or computer processors which execute software instructions which cause the processors to perform a method of the invention. For example, one or more processors in a system may implement data processing blocks in the methods described herein by executing software instructions retrieved from a program memory accessible to the processors. The invention may also be provided in the form of a program product. The program product may comprise any medium which carries a set of computer-readable instructions that, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs and DVDs, electronic data storage media including ROMs, flash RAM, or the like. The instructions may be present on the program product in encrypted and/or compressed formats.

Certain implementations of the invention may comprise transmission of information across networks, and distributed computational elements which perform one or more methods of the inventions. For example, alertness measurements or state inputs may be delivered over a network, such as a local-area-network, wide-area-network, or the internet, to a computational device that performs individual alertness predictions. Future inputs may also be received over a network with corresponding future alertness distributions sent to one or more recipients over a network. Such a system may enable a distributed team of operational planners and monitored individuals to utilize the information provided by the invention. A networked system may also allow individuals to utilize a graphical interface, printer, or other display device to receive personal alertness predictions and/or recommended future inputs through a remote computational device. Such a system would advantageously minimize the need for local computational devices.

Certain implementations of the invention may comprise exclusive access to the information by the individual subjects. Other implementations may comprise shared information between the subject's employer, commander, flight surgeon, scheduler, or other supervisor or associate, by government, industry, private organization, and/or the like, or by any other individual given permitted access.

Certain implementations of the invention may comprise the disclosed systems and methods incorporated as part of a larger system to support rostering, monitoring, selecting or otherwise influencing individuals and/or their environments. Information may be transmitted to human users or to other computerized systems.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components that are not structurally equivalent to the disclosed structure which performs the function in the illustrated exemplary embodiments of the invention. As will be apparent to those skilled in the art in the light of the foregoing disclosure, many alterations and modifications are possible in the practice of this invention without departing from the spirit or scope thereof. For example:

The systems and methods of various embodiments may be extended to include other measures of human performance such as gross-motor strength, dexterity, endurance, or other physical measures. For example, fatigue may be replaced by one or more other types of neurobehavioral performance such as "sleepiness", "alertness", "tiredness", "cognitive performance", "cognitive throughput", and/or the like.

Other models or estimation procedures may be included to deal with biologically active agents, external factors, or other identified or as yet unknown factors affecting alertness/fatigue.

In the embodiments described above, model-predicted fatigue levels and CPM values are predicted at times during a time interval of interest. Usually, such a time interval of interest is in the future, but this is not necessary. In some implementations, the time period of interest may be in the past. In such implementations, references to future data (e.g. hypothetical block 101 activity schedules) may be replaced by actual past activity schedules.

What is claimed is:

1. A method for assessing the impact of fatigue on performance, the method comprising:
   determining an initial model-predicted fatigue level of an individual at an initial time;
   creating a mapping function that that transforms a fatigue level to a contextual performance metric, wherein creating the mapping function comprises:
      selecting a set of records from a historical fatigue database, the historical fatigue database populated by records, each record comprising: a contextual performance metric field comprising a contextual performance metric value obtained from one or more historical events; and a fatigue level field comprising a fatigue level value obtained from one or more individuals associated with the one or more historical events;
      grouping the selected records into one or more zones, each zone spanning a range of fatigue levels;
      for each zone, combining the contextual performance metric values of the records grouped into the zone to determine a zone-based contextual performance metric value; and
      determining the mapping function to be one or more of: a piecewise function, a discrete function, a continuous function, a linear function, and a look-up table, that correlates fatigue levels within each fatigue zone to a corresponding zone-based contextual performance metric; and
   transforming the initial model-predicted fatigue level into an initial contextual performance metric by applying the mapping function to the initial model-predicted fatigue level.

2. A method according to claim 1 further comprising:
   determining an additional model-predicted fatigue level of the individual at an additional time, the additional time after the initial time and during a time interval of interest;
   transforming the additional model-predicted fatigue levels into an additional contextual performance metric by applying the mapping function to the additional model-predicted fatigue level.

3. A method according to claim 2 wherein determining the additional model-predicted fatigue level comprises applying a fatigue-modeling technique to predict the additional model-predicted fatigue level and wherein applying the fatigue-modeling technique is based at least in part on the initial model-predicted fatigue level.

4. A method according to claim 2 further comprising receiving schedule data for the individual in the time interval of interest, the schedule data comprising at least one of: activity schedule data relating to times during the time interval of interest that the individual is expected to be performing a particular activity; and sleep schedule data relating to times during the time interval of interest that the individual is expected to be sleeping.

5. A method according to claim 4 wherein the activity type of an incident comprises one or more of: operating a vehicle, making goods, testing goods, and performing a military activity.

6. A method according to claim 4 wherein determining the additional model-predicted fatigue level comprises applying a fatigue-modeling technique to estimate the additional model-predicted fatigue level, wherein applying the fatigue-modeling technique is based at least in part on the schedule data.

7. A method according to claim 6 wherein the time interval of interest takes place in the future and the schedule data comprises sleep schedule data which assumes that the individual will be awake during the time interval of interest.

8. A method according to claim 2 further comprising:
   receiving a plurality of hypothetical schedule data scenarios, each hypothetical schedule data scenario comprising at least one of: hypothetical activity schedule data relating to times during the time interval of interest that the individual is expected to be performing a particular activity; and hypothetical sleep schedule data relating to times during the time interval of interest that the individual is expected to be sleeping;
   for each hypothetical schedule data scenario, repeating the steps of:
      determining the additional model-predicted fatigue level; and
      transforming the additional model-predicted fatigue levels into the additional contextual performance metric;
   to thereby obtain, for each hypothetical schedule data scenario, a scenario-specific additional contextual performance metric; and
   comparing the scenario-specific additional contextual performance metrics to one another.

9. A method according to claim 8 wherein, for each hypothetical schedule data scenario, determining the additional model-predicted fatigue level comprises applying a fatigue-modeling technique to estimate the additional model-predicted fatigue level and wherein applying the fatigue-modeling technique is based at least in part on the hypothetical schedule data scenario.

10. A method according to claim 2 wherein applying the mapping function to the additional model-predicted fatigue level comprises determining the zone into which the additional model-predicted fatigue-level belongs and outputting, as the additional contextual performance metric, the corresponding zone-based contextual performance metric value.

11. A method according to claim 1 wherein determining the initial model-predicted fatigue level comprises applying a fatigue-measurement technique to obtain a current fatigue level of the individual at a current time.

12. A method according to claim 1 wherein determining the initial model-predicted fatigue level comprises applying a fatigue-modeling technique to estimate the initial model-predicted fatigue level.

13. A method according to claim 1 wherein the contextual performance metric comprises one or more of: an incident-related metric associated with a particular activity; and an incident-related metric associated with a particular environment.

14. A method according to claim 13 wherein the environment type of an incident comprises one or more of: a driver seat of a motor vehicle, a pilot seat of airplane or other air-transport vehicle, a factory setting, a particular stretch of road, a particular segment of a flight, activities occurring at night, the occurrence of activities during the day, the occurrence of activities at dusk, the occurrence of activities at dawn, and the occurrence of activities in a particular geographical region.

15. A method according to claim 1 wherein the contextual performance metric comprises one or more of: a performance metric associated with a particular activity; and a performance metric associated with a particular environment.

16. A method according to claim 1 wherein the fatigue level value from the one or more individuals associated with the one or more historical events is obtained by at least one of: applying a fatigue-measurement technique to the one or more individuals; and applying a fatigue-modeling technique to the one or more individuals.

17. A method according to claim 1 wherein one or more records populating the historical fatigue database may be created by one or more of: a manual user entry through an electronic interface, automatic entry through a networked communication interface, and extraction of entries from another database or information system.

18. A method according to claim 1 further comprising: obtaining the mapping function by selecting the mapping function from among one or more existing mapping functions previously created based on information contained in the historical fatigue database.

19. A method according to claim 1 further comprising: saving the mapping function into a mapping function database.

20. A method according to claim 1 wherein determining the mapping function comprises using a curve fitting technique to select parameters of a mathematical function such that the fatigue level values of the grouped selected records are fit to the corresponding zone-based contextual performance metric value.

21. A method according to claim 1 wherein grouping the selected records into one or more zones comprises assigning each zone a range of possible fatigue levels such that the differences between an upper and a lower boundary for each range are equal to one another.

22. A method according to claim 1 wherein the range of fatigue levels for one or more of the zones comprises a single value.

23. A method according to claim 1 wherein combining the contextual performance metric values of the records grouped into the zone to determine the zone-based contextual performance metric value comprises averaging the contextual performance metric values of the records grouped into the zone.

24. A method according to claim 1 wherein the contextual performance metric comprises one or more of:
a number of injuries associated with an incident,
a number of injuries associated with an incident occurring in a particular environment,
a number of injuries associated with an incident occurring during the performance of a particular activity,
an injury severity associated with an incident,
an injury severity associated with an incident occurring in a particular environment,
an injury severity associated with an incident occurring during the performance of a particular activity,
a cost of repair associated with an incident,
a cost of repair associated with an incident occurring in a particular environment,
a cost of repair associated with an incident occurring during the performance of a particular activity,
an increase in an insurance premium associated with an incident,
an increase in an insurance premium associated with an incident occurring in a particular environment,
an increase in an insurance premium associated with an incident occurring during the performance of a particular activity,
a performance rate while performing a particular activity,
a performance rate during a work shift,
a performance rate while performing in a particular environment,
an error rate while performing a particular activity,
an error rate during a work shift, and
an error rate while performing in a particular environment.

25. A method according to claim 1 wherein records of the historical fatigue database further comprise one or more classifier fields comprising record-classification criteria associated with the one or more historical events; and wherein selecting a set of records is based at least in part on record classification criteria in the one or more classifier fields associated with each record.

26. A method according to claim 25 wherein the record-classification criteria of at least one of the one or more classifier fields comprises an environment type of the one or more historical events.

27. A method according to claim 25 wherein the record-classification criteria of at least one of the one or more classifier fields comprises an activity type of the one or more historical events.

28. A method for assessing the impact of fatigue on performance, the method comprising:
receiving schedule data for the individual in a time interval of interest, the schedule data comprising at least one of: activity schedule data relating to times during the future time interval of interest that the individual is expected to be performing a particular activity; and sleep schedule data relating to times during the future time interval of interest that the individual is expected to be sleeping;
determining a model-predicted fatigue level of the individual at a predicted time, the predicted time during the time interval of interest;
creating a mapping function that transforms a fatigue level to a contextual performance metric, wherein creating the mapping function comprises:
selecting a set of records from a historical fatigue database, the historical fatigue database populated by records, each record comprising: a contextual performance metric field comprising a contextual performance metric value obtained from one or more historical events; and a fatigue level field comprising a fatigue level value obtained from one or more individuals associated with the one or more historical events;
grouping the selected records into one or more zones, each zone spanning a range of possible fatigue levels; and
for each zone, combining the contextual performance metric values of the records grouped into the zone to determine a zone-based contextual performance metric value;
determining the mapping function to be one or more of: a piecewise function, a discrete function, a continuous function, a linear function, and a look-up table, that correlates fatigue levels within each fatigue zone to a corresponding zone-based contextual performance metric; and transforming the model-predicted fatigue level into a contextual performance metric by applying the mapping function to the model-predicted fatigue level;

wherein determining the future model-predicted fatigue level is based at least in part on the schedule data.

29. A method for assessing the impact of fatigue on performance, the method comprising:

determining an initial model-predicted fatigue level of an individual at an initial time;

transforming the initial model-predicted fatigue level into an initial contextual performance metric by applying a mapping function to the initial model-predicted fatigue level, the mapping function based at least in part on information contained in an historical fatigue database;

determining an additional model-predicted fatigue level of the individual at an additional time, the additional time after the initial time and during a time interval of interest; and transforming the additional model-predicted fatigue levels into an additional contextual performance metric by applying the mapping function to the additional model-predicted fatigue level;

wherein the historical fatigue database is populated by records, each record comprising: a contextual performance metric field comprising a contextual performance metric value obtained from one or more historical events; a fatigue level field comprising a fatigue level value obtained from one or more individuals associated with the one or more historical events; and one or more classifier fields comprising record-classification criteria associated with the one or more historical events;

wherein transforming the additional model-predicted fatigue levels into the additional contextual performance metric comprises obtaining the mapping function by creating the mapping function based on information contained in the historical fatigue database;

wherein the mapping function is a discrete mapping function; and wherein creating the mapping function comprises:

selecting a subset of the historical fatigue database based at least in part on record classification criteria in the one or more classifier fields associated with each record;

grouping the records into a plurality of zones, each zone spanning a range of possible fatigue levels;

for each zone, combining the contextual performance metric values of the records grouped into the zone to determine a zone-based contextual performance metric value; and determining the mapping function to be one of the zone-based contextual performance metric values which depends on the zone into which the additional model-predicted level belongs.

30. A method according to claim 29 wherein grouping the records into a plurality of zones comprises assigning each zone a range of possible fatigue levels such that the differences between an upper and a lower boundary for each range are equal to one another.

31. A method according to claim 29 wherein grouping the records into a plurality of zones comprises assigning each zone a range of possible fatigue levels such that the union of all zones is contiguous.

32. A method according to claim 31 wherein combining the contextual performance metric values of the records grouped into the zone to determine the zone-based contextual performance metric value comprises averaging the contextual performance metric values of the records grouped into the zone.

33. A method according to claim 32 wherein applying the mapping function to the additional model-predicted fatigue level comprises determining the zone into which the additional model-predicted fatigue-level belongs and outputting, as the additional contextual performance metric, the corresponding zone-based contextual performance metric value.

* * * * *